United States Patent
Li et al.

(10) Patent No.: US 10,482,743 B2
(45) Date of Patent: Nov. 19, 2019

(54) FLEXIBLE TEMPERATURE SENSOR INCLUDING CONFORMABLE ELECTRONICS

(71) Applicant: MC10, Inc., Lexington, MA (US)

(72) Inventors: Xia Li, Wakefield, MA (US); Sanjay Gupta, Bedford, MA (US); Kevin J. Dowling, Westford, MA (US); Isaiah Kacyvenski, Weston, MA (US); Melissa Ceruolo, Methuen, MA (US); Barry G. Ives, Voorhees, NJ (US)

(73) Assignee: MC10, INC., Lexington, MA (US)

( * ) Notice: Subject to any disclaimer, the term of this patent is extended or adjusted under 35 U.S.C. 154(b) by 21 days.

(21) Appl. No.: 15/139,256

(22) Filed: Apr. 26, 2016

(65) Prior Publication Data

US 2016/0240061 A1    Aug. 18, 2016

Related U.S. Application Data

(63) Continuation of application No. 14/451,981, filed on Aug. 5, 2014, now Pat. No. 9,372,123.
(Continued)

(51) Int. Cl.
  *G08B 21/02*    (2006.01)
  *G08B 3/10*    (2006.01)
  (Continued)

(52) U.S. Cl.
  CPC ............ *G08B 21/02* (2013.01); *A61B 5/0004* (2013.01); *A61B 5/0008* (2013.01); *A61B 5/01* (2013.01);
  (Continued)

(58) Field of Classification Search
  CPC .......... G08B 21/02; G08B 3/10; G08B 17/06; A61B 5/0004; A61B 5/0008; A61B 5/01;
  (Continued)

(56) References Cited

U.S. PATENT DOCUMENTS 3,716,861 A    2/1973  Root
3,805,427 A    4/1974  Epstein
(Continued)

FOREIGN PATENT DOCUMENTS

EP    0585670 A2    3/1994
EP    0779059 A1    6/1997
(Continued)

OTHER PUBLICATIONS

Carvalhal et al., "Electrochemical Detection in a Paper-Based Separation Device", Analytical Chemistry, vol. 82, No. 3, (1162-1165) (4 pages) (Jan. 7, 2010).
(Continued)

*Primary Examiner* — Mohamed Barakat
(74) *Attorney, Agent, or Firm* — Nixon Peabody LLP

(57) ABSTRACT

Systems, methods, apparatus and devices are described for monitoring a property of an object or an individual, using a conformal sensor device that substantially conforms to contours of a portion of a surface of the object or the individual. The measurement includes data indicative of a property of a temperature of the portion of the surface and the degree of the conformal contact. An analysis engine is used to analyze the data and to generate at least one parameter indicative of the property of the temperature. Based on a comparison of the at least one parameter to a preset threshold, at least one alert can be issued and/or a command can be transmitted to regulate an environmental condition. The at least one alert can be indicative of a potential risk of harm to the object or individual.

35 Claims, 18 Drawing Sheets

Related U.S. Application Data

(60) Provisional application No. 61/862,448, filed on Aug. 5, 2013.

(51) Int. Cl.
| | | |
|---|---|---|
| *G01K 13/00* | (2006.01) | |
| *G01K 1/14* | (2006.01) | |
| *A61B 5/00* | (2006.01) | |
| *H04L 12/28* | (2006.01) | |
| *A61B 5/01* | (2006.01) | |
| *A61B 5/0205* | (2006.01) | |
| *G08B 17/06* | (2006.01) | |
| *A61B 5/053* | (2006.01) | |
| *A61B 5/11* | (2006.01) | |

(52) U.S. Cl.
CPC .......... *A61B 5/015* (2013.01); *A61B 5/02055* (2013.01); *A61B 5/6833* (2013.01); *A61B 5/7246* (2013.01); *A61B 5/7282* (2013.01); *A61B 5/74* (2013.01); *A61B 5/746* (2013.01); *G01K 1/14* (2013.01); *G01K 1/143* (2013.01); *G01K 13/002* (2013.01); *G08B 3/10* (2013.01); *H04L 12/2818* (2013.01); *H04L 12/2827* (2013.01); *A61B 5/053* (2013.01); *A61B 5/0531* (2013.01); *A61B 5/0537* (2013.01); *A61B 5/1118* (2013.01); *A61B 2560/0242* (2013.01); *A61B 2560/0412* (2013.01); *A61B 2562/02* (2013.01); *A61B 2562/0219* (2013.01); *A61B 2562/0271* (2013.01); *A61B 2562/046* (2013.01); *A61B 2562/12* (2013.01); *A61B 2562/164* (2013.01); *A61B 2562/166* (2013.01); *G01K 2213/00* (2013.01); *G08B 17/06* (2013.01)

(58) Field of Classification Search
CPC ... A61B 5/015; A61B 5/02055; A61B 5/6833; A61B 5/7246; A61B 5/7282; A61B 5/74; A61B 5/746; A61B 5/053; A61B 5/0531; A61B 5/0537; A61B 5/1118; A61B 2560/0242; A61B 2560/0412; A61B 2562/02; A61B 2562/0219; A61B 2562/0271; A61B 2562/046; A61B 2562/12; A61B 2562/164; A61B 2562/166; G01K 1/14; G01K 1/143; G01K 13/002; G01K 2213/00; H04L 12/2818; H04L 12/2827
See application file for complete search history.

(56) References Cited

U.S. PATENT DOCUMENTS

| | | | |
|---|---|---|---|
| 3,838,240 | A | 9/1974 | Schelhorn |
| 4,278,474 | A | 7/1981 | Blakeslee |
| 4,304,235 | A | 12/1981 | Kaufman |
| 4,416,288 | A | 11/1983 | Freeman |
| 4,658,153 | A | 4/1987 | Brosh |
| 5,272,375 | A | 12/1993 | Belopolsky |
| 5,306,917 | A | 4/1994 | Black |
| 5,326,521 | A | 7/1994 | East |
| 5,331,966 | A | 7/1994 | Bennett |
| 5,360,987 | A | 11/1994 | Shibib |
| 5,471,982 | A | 5/1995 | Edwards |
| 5,454,270 | A | 10/1995 | Brown |
| 5,491,651 | A | 2/1996 | Janic |
| 5,567,975 | A | 10/1996 | Walsh |
| 5,580,794 | A | 12/1996 | Allen |
| 5,617,870 | A | 4/1997 | Hastings |
| 5,811,790 | A | 9/1998 | Endo |
| 5,817,008 | A | 10/1998 | Rafert |
| 5,907,477 | A | 5/1999 | Tuttle |
| 6,063,046 | A | 5/2000 | Allum |
| 6,265,090 | B1 | 7/2001 | Nishide |
| 6,282,960 | B1 | 9/2001 | Samuels |
| 6,343,514 | B1 | 2/2002 | Smith |
| 6,387,052 | B1 | 5/2002 | Quinn |
| 6,410,971 | B1 | 6/2002 | Otey |
| 6,421,016 | B1 | 7/2002 | Phillips |
| 6,455,931 | B1 | 9/2002 | Hamilton |
| 6,567,158 | B1 | 5/2003 | Falcial |
| 6,626,940 | B2 | 9/2003 | Crowley |
| 6,641,860 | B1 | 11/2003 | Kaiserman |
| 6,775,906 | B1 | 8/2004 | Silverbrook |
| 6,784,844 | B1 | 8/2004 | Boakes |
| 6,965,160 | B2 | 11/2005 | Cobbley |
| 6,987,314 | B1 | 1/2006 | Yoshida |
| 7,259,030 | B2 | 8/2007 | Daniels |
| 7,265,298 | B2 | 9/2007 | Maghribi |
| 7,302,751 | B2 | 12/2007 | Hamburgen |
| 7,337,012 | B2 | 2/2008 | Maghribi |
| 7,487,587 | B2 | 2/2009 | Vanfleteren |
| 7,491,892 | B2 | 2/2009 | Wagner |
| 7,521,292 | B2 | 4/2009 | Rogers |
| 7,557,367 | B2 | 7/2009 | Rogers |
| 7,618,260 | B2 | 11/2009 | Daniel |
| 7,622,367 | B1 | 11/2009 | Nuzzo |
| 7,727,228 | B2 | 6/2010 | Abboud |
| 7,739,791 | B2 | 6/2010 | Brandenburg |
| 7,759,167 | B2 | 7/2010 | Vanfleteren |
| 7,815,095 | B2 | 10/2010 | Fujisawa |
| 7,960,246 | B2 | 6/2011 | Flamand |
| 7,982,296 | B2 | 7/2011 | Nuzzo |
| 8,097,926 | B2 | 1/2012 | De Graff |
| 8,198,621 | B2 | 6/2012 | Rogers |
| 8,207,473 | B2 | 6/2012 | Axisa |
| 8,217,381 | B2 | 7/2012 | Rogers |
| 8,320,981 | B1 * | 11/2012 | Mayer .......................... 600/310 |
| 8,372,726 | B2 | 2/2013 | De Graff |
| 8,389,862 | B2 | 3/2013 | Arora |
| 8,431,828 | B2 | 4/2013 | Vanfleteren |
| 8,440,546 | B2 | 5/2013 | Nuzzo |
| 8,536,667 | B2 | 9/2013 | De Graff |
| 8,552,299 | B2 | 10/2013 | Rogers |
| 8,618,656 | B2 | 12/2013 | Oh |
| 8,664,699 | B2 | 3/2014 | Nuzzo |
| 8,679,888 | B2 | 3/2014 | Rogers |
| 8,729,524 | B2 | 5/2014 | Rogers |
| 8,754,396 | B2 | 6/2014 | Rogers |
| 8,865,489 | B2 | 10/2014 | Rogers |
| 8,886,334 | B2 | 11/2014 | Ghaffari |
| 8,905,772 | B2 | 12/2014 | Rogers |
| 9,012,784 | B2 | 4/2015 | Arora |
| 9,082,025 | B2 | 7/2015 | Fastert |
| 9,105,555 | B2 | 8/2015 | Rogers |
| 9,105,782 | B2 | 8/2015 | Rogers |
| 9,119,533 | B2 | 9/2015 | Ghaffari |
| 9,123,614 | B2 | 9/2015 | Graff |
| 9,159,635 | B2 | 10/2015 | Elolampi |
| 9,168,094 | B2 | 10/2015 | Lee |
| 9,171,794 | B2 | 10/2015 | Rafferty |
| 9,186,060 | B2 | 11/2015 | De Graff |
| 9,226,402 | B2 | 12/2015 | Hsu |
| 9,247,637 | B2 | 1/2016 | Hsu |
| 9,289,132 | B2 | 3/2016 | Ghaffari |
| 9,295,842 | B2 | 3/2016 | Ghaffari |
| 9,324,733 | B2 | 4/2016 | Rogers |
| 9,372,123 | B2 | 6/2016 | Li |
| 2001/0012918 | A1 | 8/2001 | Swanson |
| 2001/0021867 | A1 | 9/2001 | Kordis |
| 2002/0026127 | A1 | 2/2002 | Balbierz |
| 2002/0082515 | A1 | 6/2002 | Campbell |
| 2002/0094701 | A1 | 7/2002 | Biegelsen |
| 2002/0113739 | A1 | 8/2002 | Howard |
| 2002/0128700 | A1 | 9/2002 | Cross, Jr. |
| 2002/0145467 | A1 | 10/2002 | Minch |
| 2002/0151934 | A1 | 10/2002 | Levine |
| 2002/0158330 | A1 | 10/2002 | Moon |
| 2003/0017848 | A1 | 1/2003 | Engstrom |
| 2003/0045025 | A1 | 3/2003 | Coyle |
| 2003/0097165 | A1 | 5/2003 | Krulevitch |

(56) References Cited

U.S. PATENT DOCUMENTS

| | | |
|---|---|---|
| 2003/0120271 A1 | 6/2003 | Burnside |
| 2003/0162507 A1 | 8/2003 | Vatt |
| 2003/0214408 A1 | 11/2003 | Grajales |
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0243204 A1 | 12/2004 | Maghribi |
| 2005/0021103 A1 | 1/2005 | DiLorenzo |
| 2005/0029680 A1 | 2/2005 | Jung |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2005/0248312 A1 | 11/2005 | Cao |
| 2005/0285262 A1 | 12/2005 | Knapp |
| 2006/0003709 A1 | 1/2006 | Wood |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0128346 A1 | 6/2006 | Yasui |
| 2006/0154398 A1 | 7/2006 | Qing |
| 2006/0160560 A1 | 7/2006 | Josenhans |
| 2006/0248946 A1 | 11/2006 | Howell |
| 2006/0257945 A1 | 11/2006 | Masters |
| 2006/0264767 A1 | 11/2006 | Shennib |
| 2006/0270135 A1 | 11/2006 | Chrysler |
| 2006/0286785 A1 | 12/2006 | Rogers |
| 2007/0027514 A1 | 2/2007 | Gerber |
| 2007/0031283 A1 | 2/2007 | Davis |
| 2007/0100218 A1 | 5/2007 | Sweitzer |
| 2007/0108389 A1 | 5/2007 | Makela |
| 2007/0113399 A1 | 5/2007 | Kumar |
| 2007/0123756 A1 | 5/2007 | Kitajima |
| 2007/0206655 A1* | 9/2007 | Haslett .................. A61B 5/01 374/141 |
| 2007/0270672 A1 | 11/2007 | Hayter |
| 2008/0036097 A1 | 2/2008 | Ito |
| 2008/0046080 A1 | 2/2008 | Vanden Bulcke |
| 2008/0074383 A1 | 3/2008 | Dean |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0188912 A1 | 8/2008 | Stone |
| 2008/0193749 A1 | 8/2008 | Thompson |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0287167 A1 | 11/2008 | Caine |
| 2008/0313552 A1 | 12/2008 | Buehler |
| 2009/0000377 A1 | 1/2009 | Shipps |
| 2009/0001550 A1 | 1/2009 | Yonggang |
| 2009/0015560 A1 | 1/2009 | Robinson |
| 2009/0017884 A1 | 1/2009 | Rotschild |
| 2009/0048556 A1 | 2/2009 | Durand |
| 2009/0088750 A1 | 4/2009 | Hushka |
| 2009/0105605 A1 | 4/2009 | Abreu |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0322480 A1 | 12/2009 | Benedict |
| 2010/0002402 A1 | 1/2010 | Rogers |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0034912 A1 | 2/2011 | De Graff |
| 2011/0051384 A1 | 3/2011 | Kriechbaum |
| 2011/0054583 A1 | 3/2011 | Litt |
| 2011/0101789 A1 | 5/2011 | Salter |
| 2011/0121822 A1 | 5/2011 | Parsche |
| 2011/0140897 A1 | 6/2011 | Purks |
| 2011/0175735 A1 | 7/2011 | Forster |
| 2011/0184320 A1 | 7/2011 | Shipps |
| 2011/0190746 A1* | 8/2011 | Rink .................... A61B 18/22 606/12 |
| 2011/0213559 A1 | 9/2011 | Pollack |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0277813 A1 | 11/2011 | Rogers |
| 2011/0284268 A1 | 11/2011 | Palaniswamy |
| 2011/0306851 A1 | 12/2011 | Wang |
| 2012/0016258 A1 | 1/2012 | Webster |
| 2012/0029308 A1* | 2/2012 | Paquet .................... A61B 5/01 600/301 |
| 2012/0051005 A1 | 3/2012 | Vanfleteren |
| 2012/0052268 A1 | 3/2012 | Axisa |
| 2012/0065937 A1 | 3/2012 | De Graff |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0094638 A1 | 4/2012 | Shamoon |
| 2012/0101413 A1 | 4/2012 | Beetel |
| 2012/0101538 A1 | 4/2012 | Ballakur |
| 2012/0108012 A1 | 5/2012 | Yasuda |
| 2012/0126418 A1 | 5/2012 | Feng |
| 2012/0157804 A1 | 6/2012 | Rogers |
| 2012/0172697 A1 | 7/2012 | Urman |
| 2012/0178367 A1 | 7/2012 | Matsumoto |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman |
| 2012/0327608 A1 | 12/2012 | Rogers |
| 2013/0023744 A1* | 1/2013 | Benni ............... A61B 5/14551 600/339 |
| 2013/0041235 A1 | 2/2013 | Rogers |
| 2013/0099358 A1 | 4/2013 | Elolampi |
| 2013/0100618 A1 | 4/2013 | Rogers |
| 2013/0118255 A1 | 5/2013 | Callsen |
| 2013/0150693 A1 | 6/2013 | D'angelo |
| 2013/0185003 A1 | 7/2013 | Carbeck |
| 2013/0192356 A1 | 8/2013 | De Graff |
| 2013/0200268 A1 | 8/2013 | Rafferty |
| 2013/0211761 A1 | 8/2013 | Brandsma |
| 2013/0214300 A1 | 8/2013 | Lerman |

(56) References Cited

U.S. PATENT DOCUMENTS

| | | |
|---|---|---|
| 2013/0215467 A1 | 8/2013 | Fein |
| 2013/0225965 A1 | 8/2013 | Ghaffari |
| 2013/0237150 A1 | 9/2013 | Royston |
| 2013/0245388 A1 | 9/2013 | Rafferty |
| 2013/0274562 A1 | 10/2013 | Ghaffari |
| 2013/0313713 A1 | 11/2013 | Arora |
| 2013/0316442 A1 | 11/2013 | Meurville |
| 2013/0316487 A1 | 11/2013 | De Graff |
| 2013/0316645 A1 | 11/2013 | Li |
| 2013/0320503 A1 | 12/2013 | Nuzzo |
| 2013/0321373 A1 | 12/2013 | Yoshizumi |
| 2013/0328219 A1 | 12/2013 | Chau |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rogers |
| 2014/0188426 A1 | 7/2014 | Fastert |
| 2014/0191236 A1 | 7/2014 | Nuzzo |
| 2014/0216524 A1 | 8/2014 | Rogers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora |
| 2015/0099976 A1 | 4/2015 | Ghaffari |
| 2015/0100135 A1 | 4/2015 | Ives |
| 2015/0194817 A1 | 7/2015 | Lee |
| 2015/0237711 A1 | 8/2015 | Rogers |
| 2015/0241288 A1 | 8/2015 | Keen |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |
| 2015/0335254 A1 | 11/2015 | Elolampi |
| 2015/0342036 A1 | 11/2015 | Fastert |
| 2016/0027834 A1 | 1/2016 | de Graff |
| 2016/0045162 A1 | 2/2016 | De Graff |
| 2016/0081192 A1 | 3/2016 | Hsu |
| 2016/0086909 A1 | 3/2016 | Garlock |
| 2016/0095652 A1 | 4/2016 | Lee |
| 2016/0099214 A1 | 4/2016 | Dalal |
| 2016/0099227 A1 | 4/2016 | Dalal |
| 2016/0111353 A1 | 4/2016 | Rafferty |
| 2016/0135740 A1 | 5/2016 | Ghaffari |

FOREIGN PATENT DOCUMENTS

| | | |
|---|---|---|
| EP | 1808124 A2 | 7/2007 |
| EP | 2259062 A2 | 12/2010 |
| JP | 05-087511 A | 4/1993 |
| JP | 2006-523127 A | 10/2006 |
| JP | 2007-502136 A | 2/2007 |
| JP | 2008-194323 A | 8/2008 |
| JP | 2009-170173 A | 7/2009 |
| JP | 2011-122732 A | 6/2011 |
| JP | 2013-130384 A | 7/2013 |
| WO | WO 1999/038211 A2 | 7/1999 |
| WO | WO 2005/015163 A2 | 2/2005 |
| WO | WO 2005/020551 A1 | 3/2005 |
| WO | WO 2005/122285 A2 | 12/2005 |
| WO | WO 2003/021679 A2 | 3/2006 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/059671 A1 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |
| WO | WO 2015/138712 A1 | 9/2015 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).

Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

(56) References Cited

OTHER PUBLICATIONS

Kim et al., "Electrowetting on Paper for Electronic Paper Display," ACS Applied Materials & Interfaces, vol. 2, No. 11, (3318-3323) (6 pages) (Nov. 24, 2010).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Siegel et al., "Foldable Printed Circuit Boards on Paper Substrates," Advanced Functional Materials, vol. 20, No. 1, 28-35, (8 pages) (Jan. 8, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Wikipedia, "Ball bonding" article [online]. Cited in PCT/US2015/051210 search report dated Mar. 1, 2016 with the following information "Jun. 15, 2011 [retrieved on Nov. 15, 2015}. Retrieved Dec. 18, 29 from the Internet: <URL: https://web.archive.org/web/20110615221003/hltp://en.wikipedia.org/wiki/Ball_bonding>., entire document, especially para 1, 4, 5, 6," 2 pages, last page says ("last modified on May 11, 2011").

Written Opinion corresponding to co-pending International Patent Application Serial No. PCT/2014/49769, United States Patent Office, dated Nov. 19, 2014, 7 pages.

International Search Report corresponding to co-pending International Patent Application Serial No. PCT/2014/49769, United States Patent Office, dated Nov. 19, 2014, 3 pages.

Extended European Search Report, including the Supplementary European Search Report and European Search Opinion corresponding to European Application No. 14835387.3, dated Jun. 7, 2017, 9 pages.

* cited by examiner

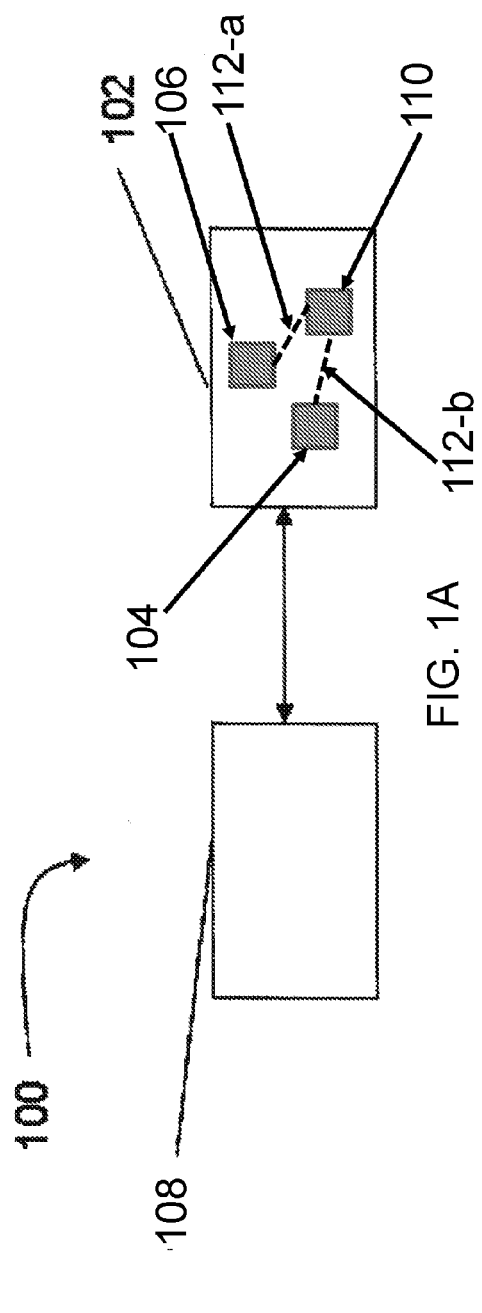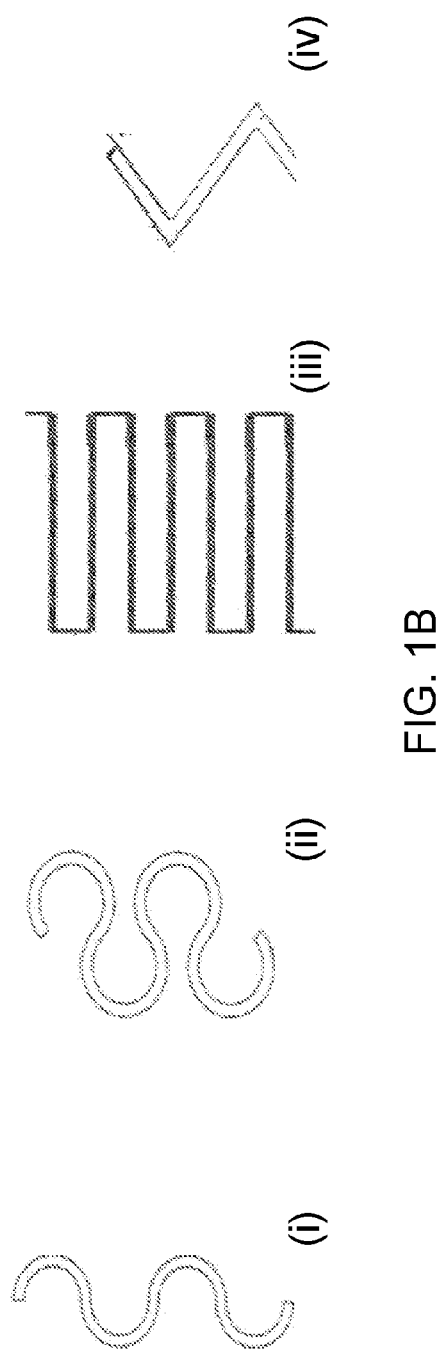

(v)

FLEXIBLE TEMPERATURE SENSOR INCLUDING CONFORMABLE ELECTRONICS

CROSS-REFERENCE TO RELATED APPLICATIONS

This application is a continuation of U.S. application Ser. No. 14/451,981, filed Aug. 5, 2014, which claims the benefit of and priority to U.S. Provisional Application No. 61/862,448, filed Aug. 5, 2013, each of which is hereby incorporated by reference herein in its entirety.

BACKGROUND OF THE DISCLOSURE

Temperature measurements can be useful for monitoring an individual's health status. For example, an elevated temperature can be indicative of a fever condition, over-exertion during exercise, a sporting event, or other physical activity, or extreme environmental conditions (including a hot vehicle). In other examples, depressed temperatures can be indicative of hypothermia.

The use of electronics in such applications can be hampered if the electronics is too boxy or rigid. The boxy, rigid electronics could affect the measurement of the softer, more pliable, and curved biological tissue.

SUMMARY OF THE DISCLOSURE

In view of the foregoing, systems and methods are provided for monitoring the temperature of an object or individual. The systems and method disclosed herein can be used to measure values indicative of temperature. In some implementations, the system can be disposed into conformal electronics that can be coupled directly to an object or individual, such as but not limited to being disposed on the skin, clothing, or protective gear. The system provides an application on a computing device for analyzing data from sensor measurements.

Example systems, methods apparatus and devices herein provide for monitoring a property of an object or an individual using a conformal sensor device mounted to a portion of a surface of the object or the individual. The system includes at least one memory for storing processor executable instructions, and a processing unit for accessing the at least one memory and executing the processor executable instructions. The processor-executable instructions include a communication module to receive data indicative of at least one measurement of at least one sensor component of the conformal sensor device, an analysis engine, and a notification component. The at least one measurement includes a measure of a property of a temperature of the portion of the surface. The conformal sensor device substantially conforms to contours of the surface to provide a degree of conformal contact, and the data indicative of the at least one measurement comprises data indicative of the degree of the conformal contact. The analysis engine includes processor-executable instructions to analyze the data indicative of at least one measurement, generate at least one parameter indicative of the property of the temperature based on the degree of the conformal contact, and compare the at least one parameter indicative of the property of the temperature to a preset threshold. T notification component includes processor-executable instructions to issue a first alert at a time $T_1$ if the at least one parameter indicative of the property of the temperature exceeds the preset threshold, and to issue a second alert at a time $T_2$ greater than $T_1$ if the at least one parameter indicative of the property of the temperature falls below the preset threshold and subsequently exceeds the preset threshold for at least a dwell time t. The second alert indicates a potential risk of harm to the object or individual.

Example systems, methods apparatus and devices herein also provide for monitoring a potential risk of harm to an object or an individual using a conformal sensor device mounted to a portion of a surface of the object or the individual. The system includes a communication interface to receive data indicative of a measurement of a sensor component of a conformal sensor device, at least one memory for storing processor executable instructions, and a processing unit for accessing the at least one memory and executing the processor executable instructions. The at least one measurement includes a measure of a property of a temperature of the portion of the surface. The conformal sensor device substantially conforms to contours of the surface to provide a degree of conformal contact, and the data indicative of the at least one measurement comprises data indicative of the degree of the conformal contact. Upon execution of the processor-executable instructions, the at least one processing unit: using the communication module, receives first data indicative of a first measurement of a first sensor component of a first conformal sensor device disposed on a first surface, and using the communication module, receives second data indicative of a second measurement of a second sensor component of a second conformal sensor device disposed on a second surface. The at least one processing unit computes, using the first data, a first parameter indicative of the first property of the first temperature based on the first degree of the conformal contact, computes, using the second data, a second parameter indicative of the second property of the second temperature based on the second degree of the conformal contact, and compares the first parameter to the second parameter. The at least one processing unit also issues a first notification if the second parameter exceeds the first parameter, and issues a second notification if at least one of the first parameter and the second parameter exceeds a preset threshold for at least a dwell time t. The first alert and/or the second alert indicates a potential risk of harm to the object or individual.

Example systems, methods apparatus and devices herein can be used to regulate an environmental condition using a conformal sensor device mounted to a portion of a surface of at least one object or individual. The system includes at least one memory for storing processor executable instructions, and a processing unit for accessing the at least one memory and executing the processor executable instructions. The processor-executable instructions include a communication module to receive data indicative of at least one measurement of at least one sensor component of the conformal sensor device, an analysis engine, and a notification component. The at least one measurement includes a measure of a property of a temperature of the portion of the surface. The conformal sensor device substantially conforms to contours of the surface to provide a degree of conformal contact, and the data indicative of the at least one measurement comprises data indicative of the degree of the conformal contact. The analysis engine includes processor-executable instructions: to analyze the data indicative of at least one measurement, to generate at least one parameter indicative of the property of the temperature based on the degree of the conformal contact, and to compare the at least one parameter indicative of the property of the temperature to a preset threshold. The notification component includes processor-executable instructions: to control the communication module to transmit a command to a controller of an environmental regulation system if the at least one parameter indicative of the property of the temperature exceeds the preset threshold. The command includes instructions to initiate the environmental regulation system and/or to modify an operating set point of the environmental regulation system.

Example systems, methods apparatus and devices herein also can be used to regulate an environmental condition using a conformal sensor device mounted to a portion of a surface of at least one object or individual. The system includes at least one memory for storing processor executable instructions, and a processing unit for accessing the at least one memory and executing the processor executable instructions. The processor-executable instructions include a communication module to receive data indicative of at least one measurement of at least one sensor component of the conformal sensor device, an analysis engine, and a notification component. The at least one measurement includes a measure of a property of a temperature of the portion of the surface. The conformal sensor device substantially conforms to contours of the surface to provide a degree of conformal contact, and the data indicative of the at least one measurement comprises data indicative of the degree of the conformal contact.

The analysis engine includes processor-executable instructions: to analyze the data indicative of at least one measurement, to generate at least one parameter indicative of the property of the temperature based on the degree of the conformal contact, and to compare the at least one parameter indicative of the property of the temperature to a preset threshold.

The notification component includes processor-executable instructions to control the communication module to transmit a command to at least one controller of an environmental regulation system: if the at least one parameter indicative of the property of the temperature exceeds the preset threshold, and if the at least one object or individual is located within a specified zone of the controller. The command comprises instructions to initiate the environmental regulation system and/or to modify an operating set point of the environmental regulation system.

The following publications, patents, and patent applications are hereby incorporated herein by reference in their entirety:

U.S. Patent Application publication no. 2010 0002402-A1, published Jan. 7, 2010, filed Mar. 5, 2009, and entitled "STRETCHABLE AND FOLDABLE ELECTRONIC DEVICES;"

U.S. Patent Application publication no. 2010 0087782-A1, published Apr. 8, 2010, filed Oct. 7, 2009, and entitled "CATHETER BALLOON HAVING STRETCHABLE INTEGRATED CIRCUITRY AND SENSOR ARRAY;"

U.S. Patent Application publication no. 2010 0116526-A1, published May 13, 2010, filed Nov. 12, 2009, and entitled "EXTREMELY STRETCHABLE ELECTRONICS;"

U.S. Patent Application publication no. 2010 0178722-A1, published Jul. 15, 2010, filed Jan. 12, 2010, and entitled "METHODS AND APPLICATIONS OF NON-PLANAR IMAGING ARRAYS;"

PCT Patent Application publication no. WO2011/084709, published Jul. 14, 2011, entitled "Methods and Apparatus for Conformal Sensing of Force and/or Change in Motion;"

U.S. Patent Application publication no. 2011 0034912-A1, published Feb. 10, 2011, filed Mar. 12, 2010, and entitled "SYSTEMS, METHODS, AND DEVICES HAVING STRETCHABLE INTEGRATED CIRCUITRY FOR SENSING AND DELIVERING THERAPY;" and PCT Patent Application no. PCT/US14/10740, filed Jan. 8, 2014, entitled "APPLICATION FOR MONITORING A PROPERTY OF A SURFACE."

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

The foregoing and other aspects, examples, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIG. 1A shows a block diagram of an example system, according to the principles herein.

DETAILED DESCRIPTION

Figure 1B:
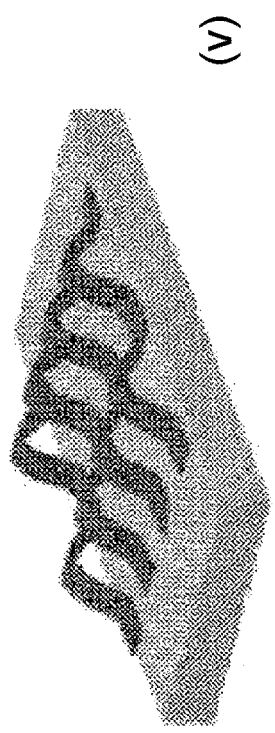
FIG. 1B shows examples of serpentine interconnects ((i) and (ii)), a boustrophedonic-shaped interconnect (iii), a zig-zag interconnect (iv), and a pop-up interconnect (v), according to the principles herein.

It should be appreciated that all combinations of the concepts described in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems for monitoring a property of a portion of an object or an individual using a conformal sensor device mounted to a portion of a surface of the object or the individual. It should be appreciated that various concepts introduced above and described in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on.

With respect to substrates or other surfaces described herein in connection with various examples, any references to "top" surface and "bottom" surface are used primarily to indicate relative position, alignment and/or orientation of various elements/components with respect to the substrate and each other, and these terms do not necessarily indicate any particular frame of reference (e.g., a gravitational frame of reference). Thus, reference to a "bottom" of a substrate or a layer does not necessarily require that the indicated surface or layer be facing a ground surface. Similarly, terms such as "over," "under," "above," "beneath" and the like do not necessarily indicate any particular frame of reference, such as a gravitational frame of reference, but rather are used primarily to indicate relative position, alignment and/or orientation of various elements/components with respect to the substrate (or other surface) and each other. The terms "disposed on" and "disposed over" encompass the meaning of "embedded in," including "partially embedded in." In addition, reference to feature A being "disposed on," "disposed between," or "disposed over" feature B encompasses examples where feature A is in contact with feature B, as well as examples where other layers and/or other components are positioned between feature A and feature B.

The disclosure relates to systems, methods and apparatus that are used for monitoring a property of an object or an individual, using a conformal sensor device mounted to a portion of a surface of the object or the individual. The conformal sensor device includes at least one sensor component for performing the measurements. The measurements can be used to provide data indicative of the temperature of a portion of the surface. The conformal sensor device is configured to substantially conform to the contours of the surface of the object or individual. The measurements include an indication of the degree of conformal contact. For example, the degree of contact can be quantified as a percentage of the surface area of the conformal sensor device that is in contact with portions of the surface of the object or the individual. In another example, the degree of contact can be quantified as a map (such as but not limited to a spatial map) of measures of the proximity of portions of the surface of the conformal sensor device with the surface of the object or the individual.

In any example implementation, the conformal sensor device can include spatially-distributed arrays of sensor components to provide a spatial mapping of the degree of conformal contact, and/or the temperature-based property, of the portion of the surface.

The measurements of the at least one sensor component provides data that can be analyzed to provide at least one parameter indicative of the property of the surface. An example system, method, and apparatus according to the principles described herein includes an analysis engine to analyze the data from the measurements to generate at least one parameter indicative of a property of the temperature of the portion of the object or individual, based on the degree of the conformal contact. The property of the temperature that is monitored using any example system, method or apparatus described herein can be at least one of a magnitude of the temperature, a spatial gradient of the temperature across the surface being monitored, and a rate of change of the temperatures with time. The analysis engine also can be configured to compare the computed parameter to a preset threshold value. The preset threshold can be determined based on the temperature-based condition being monitored.

For any of the example systems, methods, apparatus and devices described herein, the individual on which the conformal sensor device is mounted can be a human subject and/or a body part of the human subject. In some example implementations, the individual to which the conformal sensor device is associated can be a subject's head, arm, foot, chest, abdomen, and/or shoulder.

For any of the example systems, methods, apparatus and devices described herein, the object to which the conformal sensor device is associated can be an inanimate object, such as but not limited to fruits or vegetables or other produce, meat, poultry, dairy, cheese, yeast, probiotics, drug vials, biologics, or other medication. The object can be a domesticated animal, including a dog, a cat, a bird, etc., or a farm animal, including a horse, a cow, a sheep, etc. In an example implementation, the object can be a racing animal, such as but not limited to a thoroughbred horse, a dog, etc.

In an example implementation, the conformal sensor device can be used to monitor a potential risk of harm to an object or individual. As non-limiting examples, the potential harm includes a fire, a fever, a risk of heat exhaustion, heat stroke or other type of overheating (e.g., in a hot car, truck, or other compartment), improper warm-up to exercise, harmful level of athletic exertion, hypothermia, or other dangerous or undesirable health threat or dangerous physical condition. The preset threshold value can be determined as a value of the at least one parameter that is indicative of the potential risk of the harm. As a non-limiting example, the preset threshold can be a temperature that indicates a significant fever, i.e., about 100.4 F (38.0 C). As another example, a preset threshold of about 102 F can be set an indicator of a risk of heat exhaustion, heat stroke, or other type of overheating. As another example, a preset threshold of about less than 35.0° C. (95.0° F.) can be set as an indicator of a potential risk of hypothermia.

In another example implementation, the conformal sensor device can be used to regulate an environmental condition. As described herein, the measurements from the conformal sensor device disposed on or otherwise coupled to the object or individual can be analyzed, and based on the analysis, instructions can be sent to a controller of an environmental regulation system to regulate the environmental condition. The example controller can be, but is not limited to, a thermostat, a central controller, a terminal unit controller, or a building automation system. As non-limiting examples, the environmental regulation system can include at least one of a heating, ventilation and air conditioning (HVAC) system, a central air system, an air-conditioning unit, and a chiller. The preset threshold can be set based on the environmental condition being monitored, such as but not limited to a desired temperature of an environment and/or a desired humidity of the environment. The environment can be, but is not limited to, at least one room in a house, an apartment, or an office building. In any example, the preset threshold can be specified by a user or by an energy supplier.

Based on the instructions to a controller of the environmental regulation system, a digital input and/or an analog input to the environmental regulation system can be changed. As non-limiting examples, the analog input can be a voltage signal or a current signal from a variable sensing device. In an example, a digital signal can be a relay contact used to start and/or stop a component of the environmental regulation system. In an example, an analog signal can be a voltage or current signal to control the movement of the components of the environmental regulation system (such as but not limited to a valve, a damper, or a motor) that regulate the medium (such as but not limited to air, water, or steam). In an example, the instructions can be sent as a digital control program code.

In an example implementation, the environmental condition can be a level of sound (such as but not limited to music, a video, or other audible condition). The instructions sent can cause the audio-level to be reduced based on measures of a heart-rate and/or pulse-rate sensor component of the conformal sensor device. The instructions can cause the controller of the audio equipment to reduce the volume, or change the type of music, video, or other audio condition, based on the conformal sensor device measurement.

In any example implementation, two objects or individuals each may be associated with a differing preset threshold. Accordingly, in any analysis performed herein, the parameters computed for one of the objects or individuals can be compared to a first preset threshold that is different from a second preset threshold used for another of the objects or individuals. In any such example implementation, the conformal sensor device can also include an identification (ID) component with identifying information concerning the object or individual to which it is coupled. In the execution of any method herein, the identifying information of each ID component can be used to determine which preset threshold to use for the comparing made during the analysis. The identification component can be, but is not limited to, a radio-frequency identification (RFID) component.

For example, a conformal sensor device may be disposed on a body part of each individual of a group of individuals (such as but not limited to members of a family, occupants of an office building, members of an athletic team in a warm-up or exertion during play). Each individual's conformal sensor device can include an ID component that identifies the individual. In the performance of any method described herein, an example system can determine which individuals of the group occupy a room or other space, determine the preset threshold(s) to use for the comparing based on the identifying information of the ID component, and determine the type of action to take based on the comparing. As a non-limiting example, the alert(s) to send regarding the potential risk of harm to the object or individual (as described herein) can also include the identification information may include information concerning the location of each of the objects or individuals. For example, the alert(s) may indicate which individual of the group is at potential risk (e.g., due to a fever, proximity to a fire or other emergency condition, improper athletic warm-up or exertion during play) and the location of the individual. In an example, the information regarding the identity and location of the object or individual can be transmitted to an emergency service (e.g., to locate members of a family or occupants of an office building in the event of a fire, or other emergency condition, without need for any action on the part of the object or individual or any third party.)

As a non-limiting example, the location information can be provided using a global positioning system (GPS) associated with the object or individual.

As a non-limiting example, the location information can be provided using RFID readers located at known locations. For each RFID reader, a communication distance can be defined as the distance beyond which the communication signal to the given RFID reader is too low to be registered. The location information of an object or individual can be computed based on its position relative to each known RFID reader, based on the known communication distance to each RFID reader and the known RFID reader location.

In another example, the ID component can include location information that can be used to determine the location within the building of each members of the group. Instructions can be sent to an environmental regulation system to modify an environmental condition is a given area of the building based on the preset threshold associated with each of the identified objects or individuals proximate to a given location. Such instructions can be sent without any required input from a user or other individual. The instructions sent to the controller of the environmental regulation system can be to bring the environmental condition to an averaged value of a set point based on the identity and differing preset threshold values for the objects or individuals in the particular location. As a result, the an environmental regulation system may be left OFF or operate at a minimum operation setting in an unoccupied portion of a building, while the environmental regulation system at another portion may be operating at a different set point.

In another example implementation, a system, method or apparatus can be configured such that a specific type of alert causes the system to issue a notification to an emergency system as well as to caretakers. For example, the system, method or apparatus can be configured to notify a first-responder system (including nearby police, fire station, and/or ambulance), along with caretakers (such as but not limited to parents, guardians, home health attendant, and school staff or officials), in the event the analysis indicates that the potential risk of harm is imminent. As non-limiting examples, an indication of a child or elderly person in an overheating vehicle, or an indication that an individual or non-human animal is near a fire, could be set to cause such an alert to be sent to first-responders.

In another example implementation, a conformal sensor device with an ID component can be configured to provide location information through communication with smart home appliance and/or electronics whose locations are known. Individuals can have their location (i.e., which room they are in) communicated to other individuals or an emergency system through, for example, location by proximity to a smart fire/smoke detector or other electronic component in that room. For example, conformal sensor devices disposed on other types of appliances or surfaces in the home, office, or other building asset, can be used to provide such location information. In addition, the conformal sensor device can provide key information about the located individual, such as but not limited to, immediate ambient temperature, to help with rescue planning and decision making A conformal sensor device that includes sensor components to provide other types of physiological measurements can be configured to also provide information on the physical condition (vital signs) of the object or individual along with the alert.

An example system, method, and apparatus according to the principles described herein also includes a notification component. The example notification component can be used to send any of the one or more alerts and/or instructions described herein as a result of the execution of the analysis of any of the example methods, systems, or apparatus herein.

For example, the notification component can be configured to issue alerts based on any of the comparisons performed by the analysis engine. For example, the notification component can be configured to issue a first alert at a first time ($T_1$) if the comparison indicates that the computed parameter exceeds the preset threshold value. The notification component also can be configured to issue second alert at a second, later time ($T_2$) if the comparison indicates that the computed parameter falls below the preset threshold, and subsequently exceeds the preset threshold for at least a dwell time period ($t>0$).

The dwell time t also can be set based on the temperature-based condition being monitored. For example, the dwell time t can be set about equal to or below a value from medical literature that indicates the potential health threat is likely to be implicated. In various examples, the dwell time t can be about 3 minutes, about 5 minutes, about 8 minutes, or about 10 minutes.

In an example implementation, the second alert indicates the potential risk of harm to the object or individual. For example, the issuance of the second alert can indicate a likelihood of the potential health threat or safety risk existing, such as but not limited to, a fire, a fever, overheating (e.g., in a hot car, truck, or other compartment), improper exercise, or other dangerous or undesirable health or physical condition. For example, the second alert could be used to indicate that an individual (a human child or adult, or a non-human animal) is under conditions that could cause overheating, e.g., in a car, truck, or other compartment. In another example, the second alert could be used to indicate that an object (including wine, produce, or dairy products) is under conditions that could cause overheating, e.g., while being transported in a car, truck, or other compartment. In another example, the potential risk of harm is due to a potential fire emergency condition, and the second alert could be used to indicate that an individual (a human child or adult, or a non-human animal) is in the vicinity of the fire emergency.

As another example, the notification component can be configured to control a communication module to transmit a command to a controller of an environmental regulation system. For example, if the comparing indicates that the parameter indicative of the property of the temperature exceeds the preset threshold, a command can be sent that includes instructions to initiate the environmental regulation system and/or to modify the operating set point of the environmental regulation system. As another example, if the comparing indicates that the parameter indicative of the property of the temperature exceeds the preset threshold, and the object or individual associated with the conformal sensor device is located within a specified zone of the controller, the command can be sent with instructions to initiate the environmental regulation system and/or to modify the operating set point of the environmental regulation system.

An example system according to the principles herein provides for monitoring a property of an object or an individual using a conformal sensor device mounted to a portion of a surface of the object or the individual. The example system employs an application running on a mobile communication device. Non-limiting examples of such mobile communication devices include a smartphone, such as but not limited to an iphone, a BlackBerry®, or an Android™-based smartphone, a tablet, a slate, an electronic-reader (e-reader), a digital assistant, or other electronic reader or hand-held, portable, or wearable computing device, or any other equivalent device, an Xbox®, a Wii®, or other game system(s).

The conformal sensor device is communicatively coupled to the mobile communication device. The conformal sensor device includes at least one sensor component to takes measurements, such as but not limited to measurements of the temperature of a portion of the surface. The mobile communication device receives the data indicative of the measurement(s). The mobile communication device includes an application that analyzes the data to determine at least one parameter indicative of the property of the surface, such as but not limited to an indication of the temperature of the object or the individual.

FIG. 1A shows a block diagram of a non-limiting example system 100 according to the principles herein. The example system 100 includes at least one conformal sensor device 102 that includes at least one sensor component 104 to provide a measurement as described herein. For example, the measurement can be data indicative of the temperature of a portion of a surface that the at least one sensor component 104 is disposed on or coupled to. The conformal sensor device 102 can include at least one other component 106. In an example implementation, the at least one other component 106 can be another sensor component and/or a processing unit. In an example implementation, the at least one component can be configured to supply power to the conformal sensor device 102. For example, the at least one other component 106 can include a battery, or any other energy storage device, that can be used to supply a potential.

The at least one sensor component 104 includes one or more components to perform the at least one measurement. The at least one sensor component 104 can include a thermistor (including a negative temperature thermistor or a positive temperature thermistor), a thermocouple, a resistance thermometer (including a thin-film platinum resistance thermometer), a semiconductor-based temperature sensor (including a silicon bandgap temperature sensor or a p-n junction temperature sensor), an infrared temperature sensor, a chemical temperature sensor (e.g., based on a colorimetric change), or detection based on a temperature-coefficient frequency response of an oscillator (e.g., based on measurement of third harmonics).

As shown in FIG. 1A, the conformal sensor device 102 is communicatively coupled to an external computing device 108. Non-limiting examples of the computing device 108 include a smartphone (an iphone®, an Android™ phone, a Blackberry®, or other type of smartphone), a tablet, a slate, an e-reader, a game system (including a WHO or a Xbox® system), a digital assistant or other personal electronic assistant, or any other equivalent device, including any of the mobile communication devices described hereinabove.

As an example, the computing device 108 can include a processor unit that is configured to execute an application that includes an analysis module for analyzing the data signal from the conformal sensor device.

In an example implementation, the conformal sensor device 102 includes at least one notification component that is configured to transmit a signal from the apparatus to an example computing device 108. For example, the at least one component can include a transmitter or a transceiver configured to transmit a signal including data indicative of a measurement by the at least one sensor component 104 to the example computing device 108.

In an example implementation, the conformal sensor device 102 includes at least one other component 106 that is configured to transmit a signal from the apparatus to an example computing device 108. For example, the at least one component can include a transmitter or a transceiver configured to transmit a signal including data indicative of a measurement by the at least one sensor component 104 to the example computing device 108.

In an example, the at least one other component 106 can includes a sensor component configured to measure an electrical property of the surface. For example, conformal sensor device 102 can include an additional sensor to perform a capacitive-based measurement of the electrical properties of tissue, to provide a measure of the state of hydration of the tissue.

In an example, the conformal sensor device includes the at least one sensor disposed on a flexible and/or stretchable substrate. In some examples, the conformal sensor device is encapsulated in a flexible and/or stretchable encapsulant material. According to the principles herein, the substrate and/or encapsulant can include one more of a variety of polymers or polymeric composites, including polyimides, polyesters, a silicone or siloxane (e.g., polydimethylsiloxane (PDMS)), a photo-patternable silicone, a SU8 or other epoxy-based polymer, a polydioxanone (PDS), a polystyrene, a parylene, a parylene-N, an ultrahigh molecular weight polyethylene, a polyether ketone, a polyurethane, a polyactic acid, a polyglycolic acid, a polytetrafluoroethylene, a polyamic acid, a polymethyl acrylate, or any other flexible or stretchable materials, including compressible aerogel-like materials, and amorphous semiconductor or dielectric materials. In some examples described herein, the conformal sensor device can include non-flexible electronics disposed on the substrate or disposed between flexible or stretchable layers. In another non-limited example, the substrate and/or encapsulant can be formed from a silicone such as but not limited to SORTACLEAR® silicone, SOLARIS® silicone, or ECOFLEX® silicone (all available from Smooth-On, Inc., Easton, Pa.). In an example, the encapsulation layer has a Young's modulus of about 100 MPa or less.

As shown in the non-limiting example of FIG. 1A, the conformal sensor device 102 includes at least one processor unit 110, and at least one stretchable interconnect. As shown in FIG. 1A, the conformal sensor device 102 can include at least one stretchable interconnect 112-a to couple the at least one sensor component 104 to the at least one processor unit 110 and/or at least one stretchable interconnect 112-b to couple the at least one processor unit 110 to the at least one other component 106. As described herein, the at least one other component 106 can be any one or more of: a battery, a transmitter, a transceiver, an amplifier, a processing unit, a charger regulator for a battery, a radio-frequency component, a memory, and an analog sensing block.

The at least one stretchable interconnect 112-a, 112-b can be configured to have any conformation that facilitates stretchability. As shown in FIG. 1B, stretchable interconnect 112-a, 112-b can be a serpentine interconnect (FIG. 1B (i) or (ii)), a boustrophedonic-shaped interconnect (FIG. 1B (iii)), a zig-zag interconnect (FIG. 1B (iv)), and a zig-zag interconnect (FIG. 1B (iv)), according to the principles herein. In various non-limiting examples, the conformal sensor device 102 can include one or more of a serpentine interconnect, a zig-zag interconnect, a rippled interconnect, a buckled interconnect, a helical interconnect, a boustrophedonic interconnect, a meander-shaped interconnect, a pop-up interconnect, a curved interconnect, a wavy interconnect, or any other interconnect conformation that facilitates stretchability.

In an example, at least one stretchable interconnect can be formed from an electrically conductive material. In another example, the stretchable interconnect can include an electrically non-conductive material that encapsulates at least a portion of the electrically conductive material. In an example, the stretchable interconnect can be formed from a non-conductive material that can be used to provide some mechanical stability and/or mechanical stretchability between components of the conformal electronics (e.g., between device components). As a non-limiting example, the non-conductive material can be formed based on a polyimide.

In any of the examples described herein, the electrically conductive material (such as but not limited to the material of the electrical interconnect and/or the electrical contact) can be, but is not limited to, a metal, a metal alloy, a conductive polymer, or other conductive material. In an example, the metal or metal alloy of the coating may include but is not limited to aluminum, stainless steel, or a transition metal, and any applicable metal alloy, including alloys with carbon. Non-limiting examples of the transition metal include copper, silver, gold, platinum, zinc, nickel, titanium, chromium, or palladium, or any combination thereof. In other non-limiting examples, suitable conductive materials may include a semiconductor-based conductive material, including a silicon-based conductive material, indium tin oxide or other transparent conductive oxide, or Group III-IV conductor (including GaAs). The semiconductor-based conductive material may be doped.

In any of the example devices according to the principles described herein, the non-conductive material (such as but not limited to the material of a stretchable interconnect) can be formed from any material having elastic properties. For example, the non-conductive material can be formed from a polymer or polymeric material. Non-limiting examples of applicable polymers or polymeric materials include, but are not limited to, a polyimide, a polyethylene terephthalate (PET), a silicone, or a polyeurethane. Other non-limiting examples of applicable polymers or polymeric materials include plastics, elastomers, thermoplastic elastomers, elastoplastics, thermostats, thermoplastics, acrylates, acetal polymers, biodegradable polymers, cellulosic polymers, fluoropolymers, nylons, polyacrylonitrile polymers, polyamide-imide polymers, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulphone based resins, vinyl-based resins, or any combinations of these materials. In an example, a polymer or polymeric material herein can be a DYMAX® polymer (Dymax Corporation, Torrington, Conn.). or other UV curable polymer, or a silicone such as but not limited to ECOFLEX® (BASF, Florham Park, N.J.).

In an example, the conformal sensor device 102 can include at least one sensor component 104, such as but not limited to a temperature sensor. The at least one sensor component 104 can include an accelerometer and/or a gyroscope. In such examples, the accelerometer and/or gyroscope can be commercially available, including "commercial off-the-shelf" or "COTS." The accelerometers may include piezoelectric or capacitive components to convert mechanical motion into an electrical signal. A piezoelectric accelerometer may exploit properties of piezoceramic materials or single crystals for converting mechanical motion into an electrical signal. Capacitive accelerometers can employ a silicon micro-machined sensing element, such as a micro-electrical-mechanical system, or MEMS, sensing element. A gyroscope can facilitate the determination of refined location and magnitude detection. As a non-limiting example, a gyroscope can be used for determining the tilt or inclination of the object to which it is coupled. As another example, the gyroscope can be used to provide a measure of the rotational velocity or rotational acceleration of the object. For example, the tilt or inclination can be computed based on integrating the output (i.e., measurement) of the gyroscope.

In an example, the conformal sensor device 102 can include two or more sensor components to perform the measurements. At least one of the sensor components is configured to perform a measurement at the portion of the surface of the object or individual. At least one of the sensor components is configured to perform a measurement of the environment of the object or individual. For example, in a single conformal sensor device, at least one sensor component can be configured to face the direction of the surface of the object or individual, and another of the sensor components can be configured to face outwards, to perform a measurement of ambient environmental conditions.

In an example, the conformal sensor device can be configured to operate to continually measure an environmental condition as well as the measurement data of the object or individual. As a non-limiting example, the conformal sensor device can be configured to include a sensor component to perform biometric parameter sensing as well as a sensor component to perform ambient condition measurement. In an example, these two types of sensors can face opposite sides of the conformal sensor device, and the conformal sensor device is applied to the surface of the object or individual such that the environmental condition sensor component face away from the surface. In an implementation where the same type of sensor component can be used to perform the different measurements, the example conformal sensor device can be worn with either side facing the surface of the conformal sensor device, while the conformal sensor device substantially conforms to a contour of the surface of the object or individual. The side of the conformal sensor device with the sensor components facing up (i.e. away from the skin) is configured to measure data of the ambient environmental condition in the immediate vicinity of the conformal sensor device; while the side with the sensor components facing down (i.e., facing and touching the skin) is configured to measure data of the object or individual, e.g., a measurements of a human body through the human skin.

Figure 2:
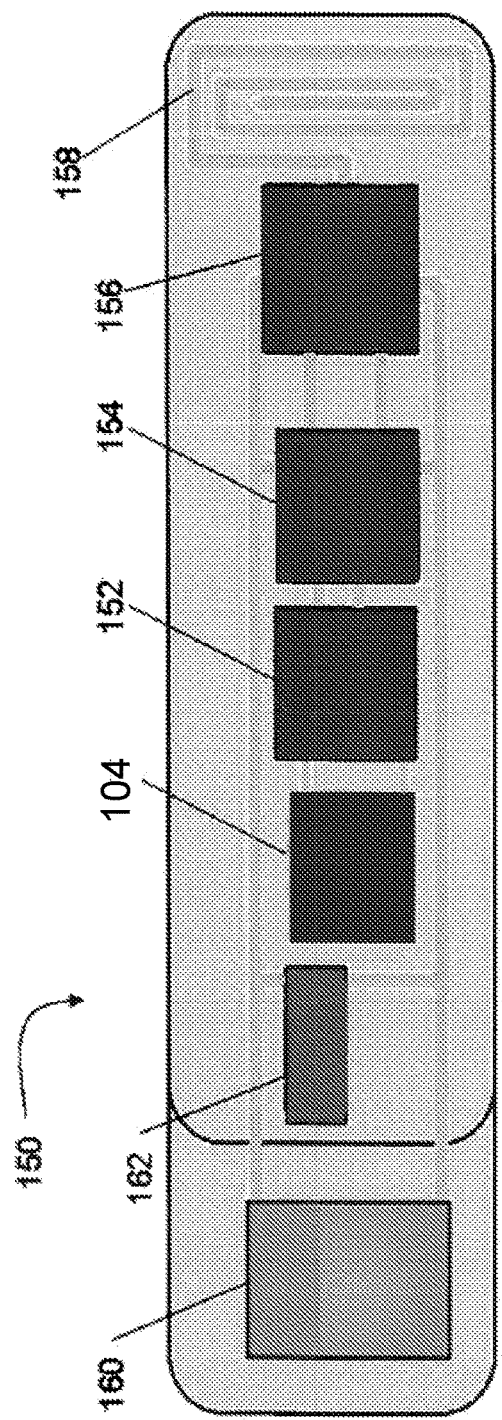
FIG. 2 shows a block diagram of an example conformal sensor device, according to the principles herein.

FIG. 2 shows a block diagram of a non-limiting example conformal sensor device 150 according another implementation of the principles herein. The example system 150 includes at least one sensor component 104 that can be used to perform a measurement. The measurement can be of a temperature of a portion of the surface. In some examples, the measurement can also be of an amount of exposure of a surface to electromagnetic radiation, or of the electrical properties of the surface through a capacitive-based measurement. In the non-limiting example of FIG. 2, the at least one other component includes an analog sensing block 152 that is coupled to the at least one sensor component 104 and at least one processor unit 154 that is coupled to the analog sensing block 152. The at least one other component includes a memory 156. For example, the memory 156 can be a non-volatile memory, such as but not limited to a flash memory, an EEPROM, or a FeRAM. As a non-limiting example, the memory 156 can be mounted as a portion of a radio-frequency (RF) chip. The at least one other component also includes a transmitter or transceiver 158. The transmitter or transceiver 158 can be used to transmit data from the at least one sensor component 104 to the example computing device 108 (not shown). The example system 150 of FIG. 2 also includes a battery 160 and a charge regulator 162 coupled to battery 160. The charge regulator 162 and battery 160 are coupled to the processor unit 154 and memory 156.

A non-limiting example use of system 150 is as follows. Battery 160 provides power for the apparatus 102 to perform the measurements. The processor unit 154 activates periodically, stimulates the analog sensing block 152, which conditions the signal and delivers it to an A/D port on the processor unit 154. The data from apparatus 102 is stored in memory 156. In an example, when a near-field communication (NFC)-enabled computing device 108 (not shown) is brought into proximity with the system 150, data is transferred to the handheld device, where it is interpreted by application software of the handheld device. The data logging and data transfer can be asynchronous. For example, data logging can occur each minute while data transfer may occur episodically.

Figure 3:
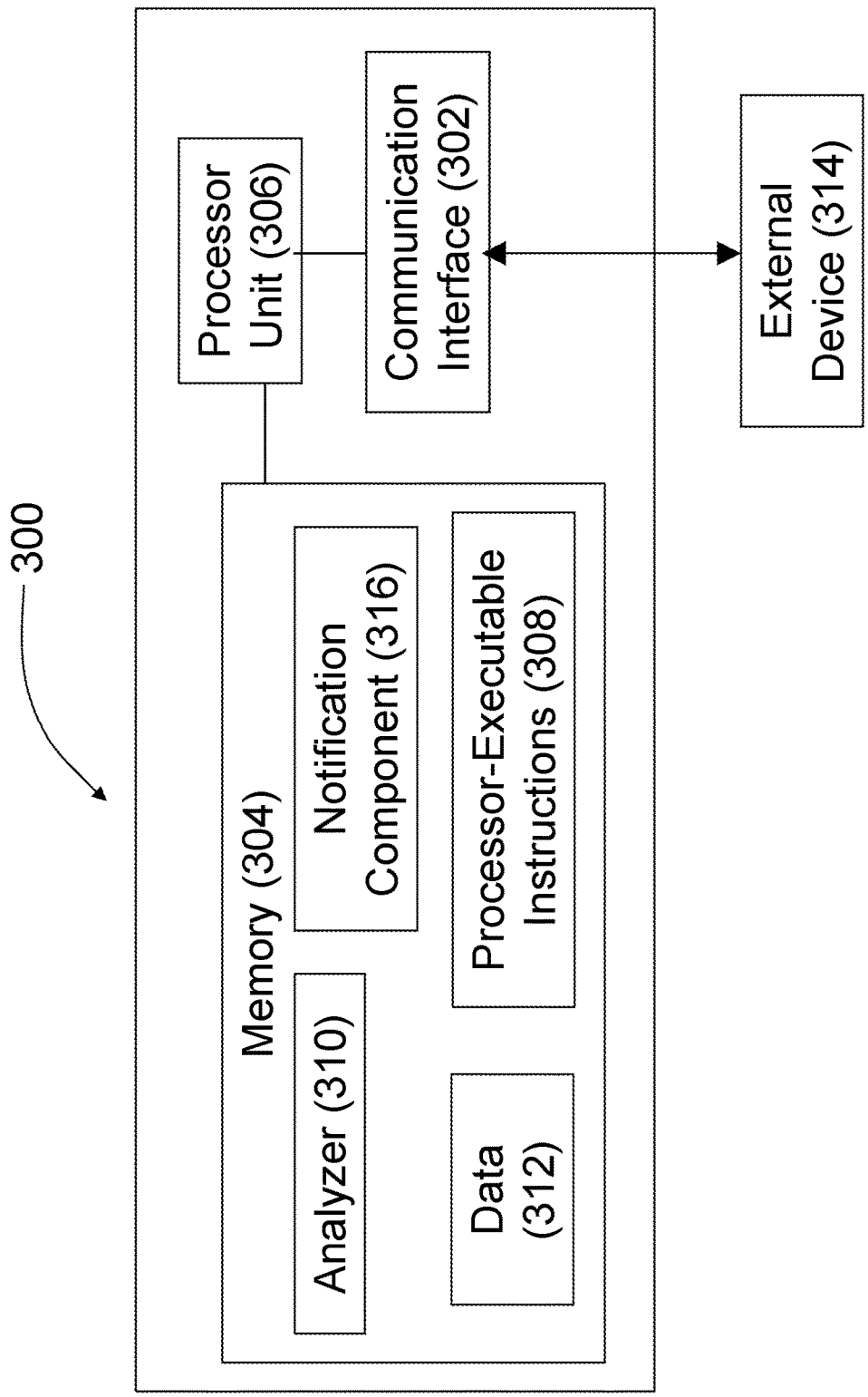
FIG. 3 shows an example apparatus, according to the principles herein.

FIG. 3 shows an example apparatus 300 that can be used to implement any of the example methods described herein. The example apparatus can be housed in the conformal sensor device 102 or the external computing device 108. The apparatus 300 includes at least one communication interface 302, at least one memory 304, and at least one processing unit 306. The at least one processing unit 306 is communicatively coupled to the at least one communication interface 302 and the at least one memory 304.

The at least one memory 304 is configured to store processor-executable instructions 308, an analyzer 310, and data 312. In this example implementation of apparatus 300, the analyzer 310 includes an analysis engine to execute processor-executable instructions to analyze the data indicative of at least one measurement, to generate at least one parameter indicative of the property of the temperature based on the degree of the conformal contact, and to compare the at least one parameter indicative of the property of the temperature to a preset threshold. At least a portion of the data representative of the at least one measurement or the at least one parameter may be stored as data 312 on the at least one memory 304 or may be stored externally to the apparatus, e.g., at an external device 314 (which may include data storage in the cloud).

In an example, the external device 314 may be an external computing device and/or the cloud (e.g., a server), including any example external computing device described herein.

In a non-limiting example, the at least one processing unit 306 executes the processor-executable instructions 308 stored in the memory 304 to generate at least one parameter indicative of the property of the temperature based on the degree of the conformal contact, and to compare the at least one parameter indicative of the property of the temperature to a preset threshold, using the analyzer 310. The at least one processing unit 306 also can execute processor-executable instructions 308 to control the communication interface 302 to communicate to the external device 314, and/or control the memory 304 to store, at least one of the generated at least one parameter, and/or data indicative of the results of the comparison of the at least one parameter indicative of the property of the temperature to the preset threshold.

The at least one memory 304 also can be configured to store a notification component 316. The notification component 316 can be configured to execute processor-executable instructions to issue a first alert at a first time ($T_1$) if the comparison indicates that the computed at least one parameter exceeds the preset threshold value. The notification component 316 also can be configured to issue second alert at a second, later time ($T_2$) if the comparison indicates that the computed parameter falls below the preset threshold, and subsequently exceeds the preset threshold for at least a dwell time period (t>0).

The first alert and/or second alert can be provided to the user using any form of sensory mode, e.g., via a visual indication (e.g., on a display), using an auditory tone (e.g., a ring, a horn, a chime or any other auditory mechanism), or using a tactile mechanisms (e.g., a vibration).

In an example implementation of apparatus 300, notification component 316 can be configured to issue the alerts based on categorizing the computed value of the at least one parameter relative to the preset threshold. The notification component 316 can be configured to define a first bin, created for the preset threshold, and increment the count in the first bin when the comparison indicates that the at least one parameter exceeds the preset threshold value (time $T_1$). Once the first bin is incremented, the notification component 316 can be configured to issue the first alert. A second bin is configured based on monitoring a time interval measured from the time $T_1$ that the count in the first bin is incremented. The second bin is configured to be incremented at a time $T_1$ later than $T_1$ (i.e., $T_1 > T_1$) if the comparison indicates that the at least one parameter falls below the preset threshold and once again exceeds the preset threshold value. One or more additional bins may be configured based on time intervals measured from the time $T_1$ that the count in the second bin is incremented. The one or more additional bins can be configured to increment over regular time intervals if the comparison indicates that the at least one parameter remains in excess of the preset threshold value. That is, the one or more additional bins are used to monitor the dwell time t. The notification component 316 is configured to issue the second alert at a time $T_2$, where $T_2 > T_i$, if the incrementing of the one or more additional bins indicates that the dwell time t is reached or exceeded. The second alert is used to indicate a potential risk of harm to the object or individual.

In another example implementation, the analyzer 310 can be configured to compare parameters computed as described herein based on two separate sensor measurements. The measurements can be based on conformal sensor devices disposed on or otherwise coupled to differing portions of a single object or body part of an individual. The measurements can be based on conformal sensor devices disposed on differing objects or individuals. In this example, the analyzer 310 is configured to compute a first parameter based on data indicative of a first measurement, to compute a second parameter based on data indicative of a second measurement, and to compare the first parameter to the second parameter. The notification component 316 can be configured to issue a first notification if the second parameter exceeds the first parameter. The notification component 316 can be configured to issue a second notification if the first parameter or the second parameter exceeds the preset threshold for at least a dwell time t. The first alert and/or the second alert indicates a potential risk of harm to the object or individual. In this example, the notification component 316 can be configured to define a first bin and a second bin. The count in the second bin can be incremented if the comparison indicates that the second parameter exceeds the first parameter, and the incrementing causes the first alert to be issued. The count in the first bin or second bin can be incremented if the comparison indicates that the first parameter or the second parameter, respectively, exceeds the preset threshold value for the defined dwell time t, and the incrementing causes the second alert to be issued.

Figure 4:
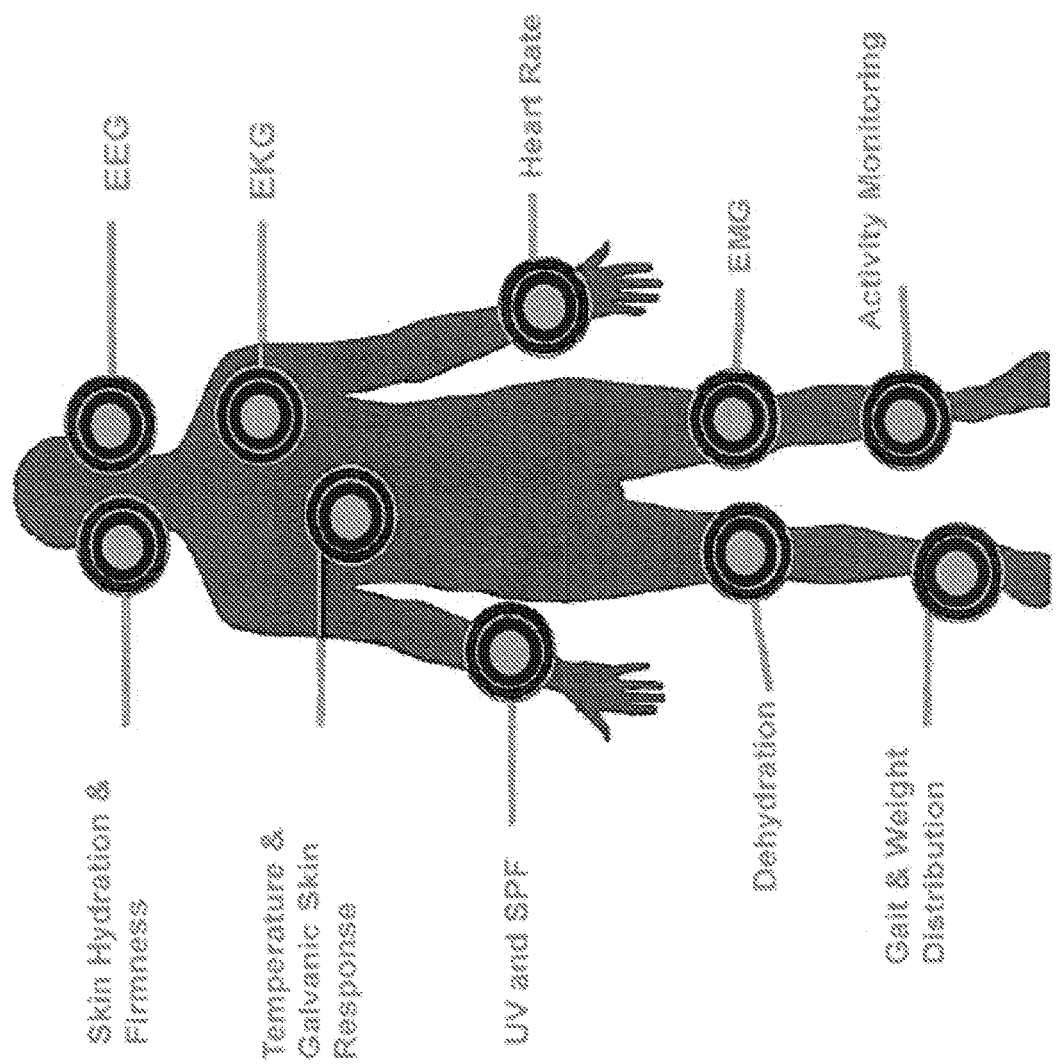
FIG. 4 shows examples of properties of an individual that may be monitored, according to the principles herein.

An example conformal sensor device according to the principles described herein can be used to monitor the properties as described hereinabove in conjunction with a wide range of other types of on-body sensors. Non-limiting examples of additional properties that may be monitored using one or more of the conformal sensor devices described herein are shown in FIG. 4. For example, an example conformal sensor device herein can include at least one sensor component according to the principles herein for measuring an amount of IR, visible or UV light exposure of the tissue, or an amount of sun protection factor (SPF) provided by a product applied to the tissue. As yet another example, an apparatus herein can be configured to include at least one hydration sensor for measuring a hydration level of the tissue.

The apparatus and systems of the technology platform described herein support conformal electronics that can be used to log sensor data at very low power levels over extended periods, while providing wireless communication with external computing devices (including handheld devices). The conformal electronics include on-body electronics and electronics that conform to other surfaces, including paper, wood, leather, fabric (including artwork or other works on canvas), a plant or a tool.

In an example, the conformal electronics technology platform described herein also may include electronic device components that can be used to monitor an amount of electromagnetic radiation that a surface is exposed to. In an example, the sensor components are UV sensors that allow the continuous recording of UVA and UVB exposure. In a non-limiting example, an example conformal sensor device described herein can be configured as a IR/visible/UV sensor that records the amount of electromagnetic radiation that a surface is exposed to, and transmits the data measurement to the example computing device.

In an example, any sensor device described in U.S. patent application Ser. No. 13/603,290, filed Sep. 4, 2012, entitled "ELECTRONICS FOR DETECTION OF A CONDITION OF TISSUE" or U.S. patent application Ser. No. 13/631,739, filed Sep. 28, 2012, entitled "ELECTRONICS FOR DETECTION OF A PROPERTY OF A SURFACE," each of which is incorporated herein by reference in its entirety including drawings, can be implemented as a conformal sensor device according to the principles of any of the examples described herein.

In a non-limiting example, a conformal sensor device according to any of the principles described herein can be mounted to the surface as a part of a patch. The surface can be a part of a surface of paper, bottles or other packaging, wood, leather, fabric, including artwork or other works on canvas, a plant or a tool.

Figure 5:
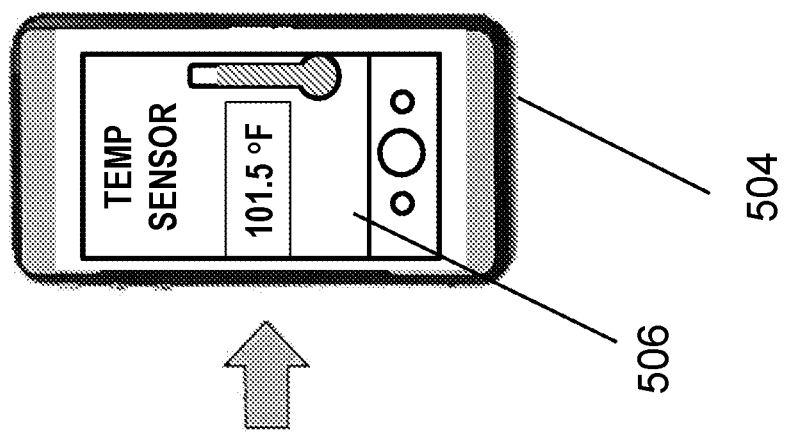
FIG. 5 shows an example patch, according to the principles herein.
Figure 5:
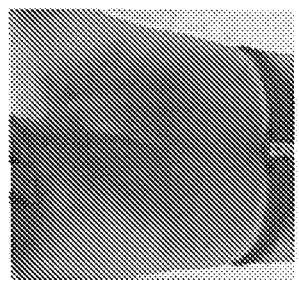
Figure 5:
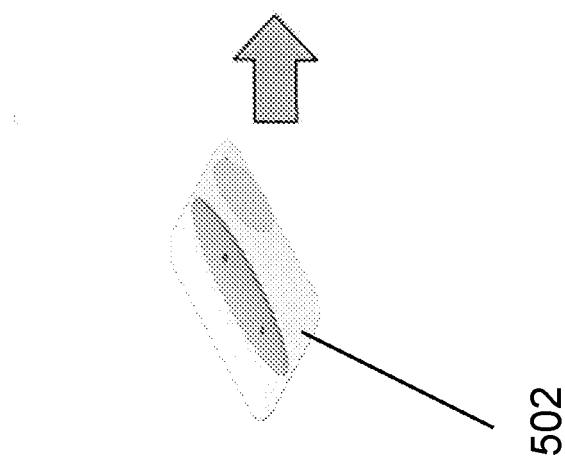

FIG. 5 shows an example of a patch 502 that can include at least one of any of the apparatus described herein. The patch 502 may be applied to the surface, such as but not limited to a portion of skin. An example computing device 504 can be used to receive the data in connection with the measurement(s) performed by the example conformal sensor device of the patch 502. For example, the patch 502 can include a transmitter or transceiver to transmit a signal to the example computing device 504.

In any example herein, the transmission of the data from the conformal sensor device to the computing device may be dependent on their proximity to each other. For example, the computing device may be configured to receive the data when the computing device is within a few centimeters of the conformal sensor device. A user may facilitate the transfer of data from the conformal sensor device (including one disposed on a patch) by positioning the computing device in proximity to the conformal sensor device.

As described in greater detail below, the computing device can include an application (an "App") to perform such functionalities as analyzing the data. For example, the data from the at least one sensor component can be analyzed as described herein by a processor executing the App on the example computing device 504 to provide the indication of the property of the object or individual. FIG. 5 shows an example display 506 of the results of data analysis using an analyzer as described herein. The analysis of the data can provide at least one parameter indicative of a temperature of the object or individual.

In some examples, the App can be implemented to log and/or to track the at least one parameter over time. For example, the App can be implemented to log and/or to track the temperature of the surface based on episodic sensor measurements over time. That is, the App on the computing device can include processor-executable instructions such that a processor unit of the computing device implements an analysis engine to analyze data indicative of a temperature measurement from the conformal sensor device of the patch 502 and provide at least one parameter indicative of a property of the object or individual.

The example patch 502 can be configured to perform temperature-based measurements to monitor the temperature of the object or individual. The data from the measurements can be collected and analyzed as described hereinabove. The analyzer can be included as a component of the patch and/or as a capability of the App. The notification component can be included as a component of the patch and/or as a capability of the App.

In an example implementation, at various time intervals, e.g., throughout the day, a NFC-enabled computing device can be placed in proximity to the patch 502 to gather the data from the measurements.

In an example, the example patch 502 may be a durable sensor patch or a disposable adhesive patch that is configured for comfort and breathability. After use, such as at the end of the day, a user may dispose of the disposable adhesive patch, and retain the durable sensor patch for reuse at a later time. The sensor patch can be re-charged using a charging pad.

Figure 6:
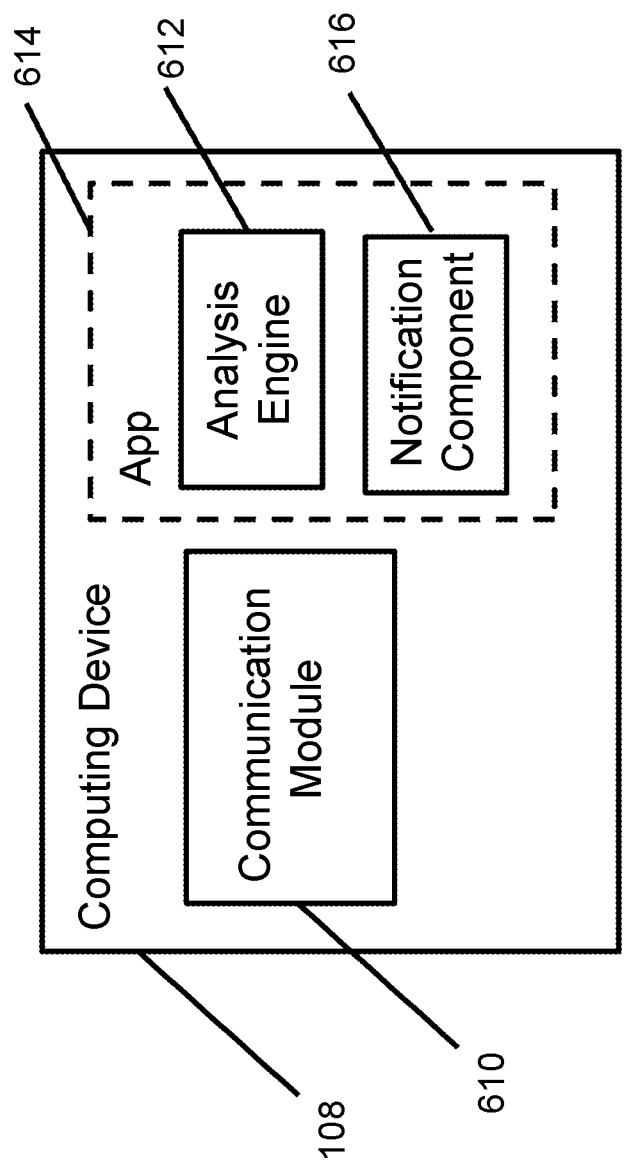
FIG. 6 shows a block diagram of an example computing device, according to the principles herein.

As shown in FIG. 6, the example computing device 108 can include a communication module 610 and an analysis engine 612. The communication module 610 can be implemented to receive data indicative of a measurement of the at least one sensor component of the conformal sensor device. The analysis engine 612 can be implemented to analyze the data to generate at least one parameter indicative of the property of the surface and the degree of the conformal contact. As shown in the example of FIG. 6, the computing device 108 can include processor-executable instructions such that a processor unit can execute an application (an App) 614 that a user can implement to initiate the analysis engine 612. The App 614 also can be configured such that a notification component 616 is initiated based on the initiation of the data analysis. Notification component 616 is configured to issue the alerts based on the data analysis and comparison to preset threshold(s) as described herein. In an example, the processor-executable instructions can include software, firmware, or other instructions.

The example communication module 610 can be configured to implement any wired and/or wireless communication interface by which information may be exchanged between the conformal sensor device 102 and the computing device 108. Non-limiting examples of wired communication interfaces include, but are not limited to, USB ports, RS232 connectors, RJ45 connectors, and Ethernet connectors, and any appropriate circuitry associated therewith. Non-limiting examples of wireless communication interfaces may include, but are not limited to, interfaces implementing Bluetooth® technology, Wi-Fi, Wi-Max, IEEE 802.11 technology, radio frequency (RF) communications, Infrared Data Association (IrDA) compatible protocols, Local Area Networks (LAN), Wide Area Networks (WAN), and Shared Wireless Access Protocol (SWAP).

In any example herein, the App 614 on the computing device 108 can include processor-executable instructions such that the analysis engine analyzes the measurements from the conformal sensor device to provide the at least one parameter, such as but not limited to, data representative of a temperature-based property of an object or an individual. In some examples, the App 614 can include processor-executable instructions to issue the alerts based on the analysis as described herein.

Figure 7:
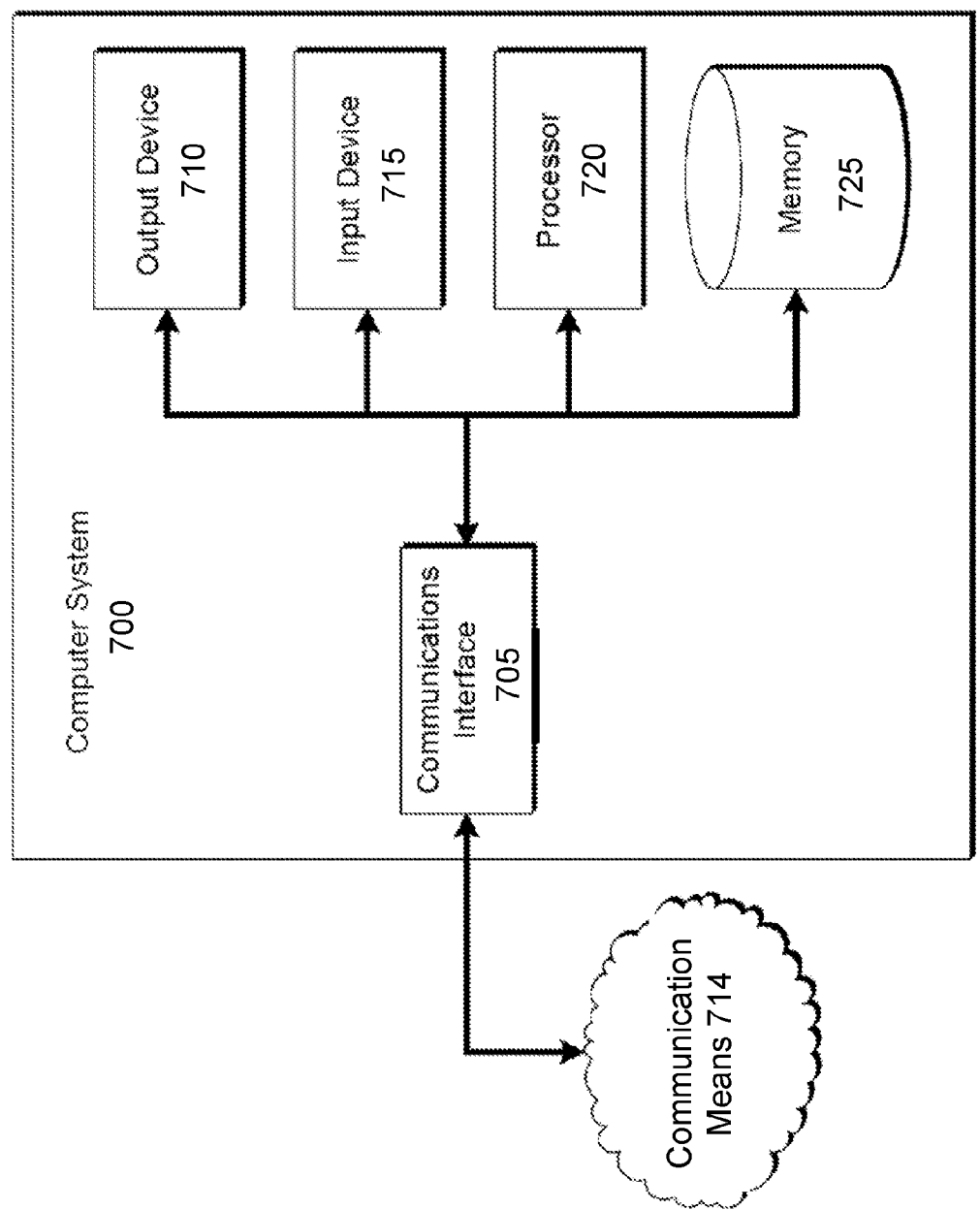
FIG. 7 shows the architecture of an example computer system, according to the principles herein.

FIG. 7 shows the general architecture of an example computer system 700 that may be employed to implement any of the example systems and methods described herein. The computer system 700 of FIG. 7 includes one or more processors 720 communicatively coupled to at least one memory 725, one or more communications interfaces 705, and one or more output devices 710 (e.g., one or more display units) and one or more input devices 715.

In the computer system 700 of FIG. 7, the memory 725 may include any computer-readable storage medium, and may store computer instructions such as processor-executable instructions for implementing the various functionalities described herein for respective systems, as well as any data relating thereto, generated thereby, or received via the communications interface(s) or input device(s). The processor(s) 720 shown in FIG. 7 may be used to execute instructions stored in the memory 725 and, in so doing, also may read from or write to the memory various information processed and or generated pursuant to execution of the instructions.

The processor 720 of the computer system 700 shown in FIG. 7 also may be communicatively coupled to or control the communications interface(s) 705 to transmit or receive various information pursuant to execution of instructions. For example, the communications interface(s) 705 may be coupled to a communication means 714, such as but not limited to a wired or wireless network, bus, or other communication means, and may therefore allow the computer system 700 to transmit information to and/or receive information from other devices (e.g., other computer systems). While not shown explicitly in the system of FIG. 7, one or more communications interfaces facilitate information flow between the components of the system 700. In some example implementations, the communications interface(s) may be configured (e.g., via various hardware components or software components) to provide a website as an access portal to at least some aspects of the computer system 700.

The output devices 710 of the computer system 700 shown in FIG. 7 may be provided, for example, to allow various information to be viewed or otherwise perceived in connection with execution of the instructions. The input device(s) 715 may be provided, for example, to allow a user to make manual adjustments, make selections, enter data or various other information, or interact in any of a variety of manners with the processor during execution of the instructions.

Examples of the systems, methods and operations described herein can be implemented in digital electronic circuitry, or in computer software, firmware, or hardware, including the structures disclosed in this specification and their structural equivalents, or in combinations of one or more thereof. Examples of the systems, methods and operations described herein can be implemented as one or more computer programs, i.e., one or more modules of computer program instructions, encoded on computer storage medium for execution by, or to control the operation of, data processing apparatus. The program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, USB memory devices, or other storage devices).

The operations described in this specification can be implemented as operations performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, firmware, script, application or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), for example. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, examples of the subject matter described in this specification can be implemented on a computer having a display device, e.g., a CRT (cathode ray tube), plasma, or LCD (liquid crystal display) monitor, for displaying information to the user and a keyboard and a pointing device, e.g., a mouse, touch screen or a trackball, by which the user can provide input to the computer. Other kinds of devices can be used to provide for interaction with a user as well; for example, the alerts and/or other feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

In some examples, a system, method or operation herein can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Example computing system 700 can include clients and servers. A client and server are generally remote from each other and typically interact through a communication network. The relationship of client and server arises by virtue of computer programs running on the respective computers and having a client-server relationship to each other. In some embodiments, a server transmits data to a client device (e.g., for purposes of displaying data to and receiving user input from a user interacting with the client device). Data generated at the client device (e.g., a result of the user interaction) can be received from the client device at the server.

Figure 8A:
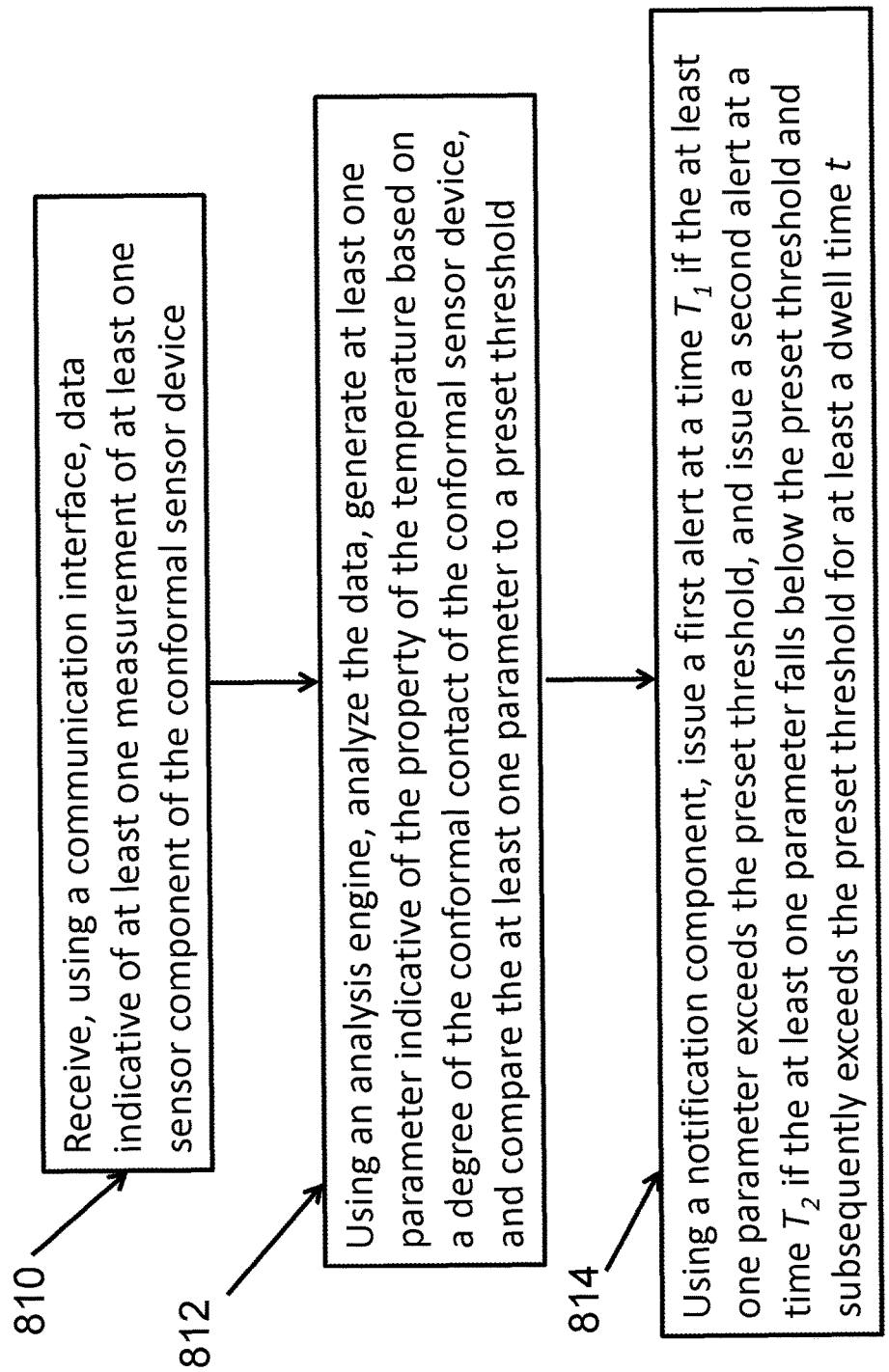
FIG. 8A shows a flowchart of an example method, according to the principles herein.

FIG. 8A shows an example method that can be implemented using any of the example systems, apparatus and devices herein. The example method can be used to monitor a property of an object or an individual using a conformal sensor device mounted to a portion of a surface of the object or the individual. The method includes receiving 810 using a communication interface, data indicative of at least one measurement of at least one sensor component of the conformal sensor device. The conformal sensor device includes at least one sensor component to obtain the at least one measurement of a property of a temperature of the portion of the surface. The conformal sensor device substantially conforms to contours of the surface to provide a degree of conformal contact. The method includes using 812 an analysis engine to analyze the data, to generate at least one parameter indicative of the property of the temperature based on a degree of the conformal contact of the conformal sensor device, and compare the at least one parameter to a preset threshold. The method includes using a notification component 814 to issue a first alert at a time $T_1$ if the at least one parameter exceeds the preset threshold, and to issue a second alert at a time $T_2$ if the at least one parameter falls below the preset threshold and subsequently exceeds the preset threshold for at least a dwell time t. The second alert provides an indication a potential risk of harm to the object or individual.

Figure 8B:
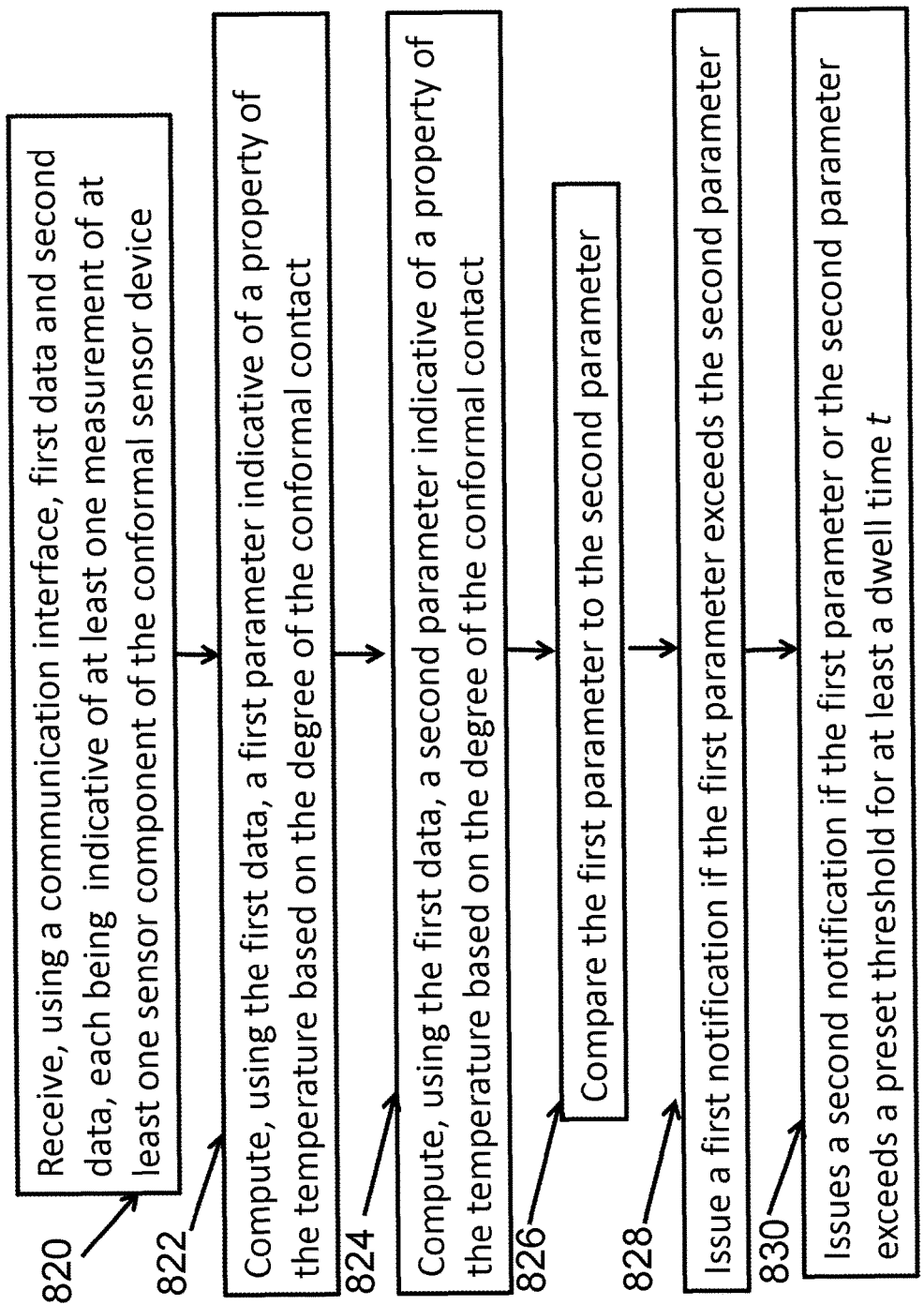
FIG. 8B shows a flowchart of another example method, according to the principles herein.

FIG. 8B shows another example method that can be implemented using any of the example systems, apparatus and devices herein. The example method can be used to monitor a property of an object or an individual using a conformal sensor device mounted to a portion of a surface of the object or the individual. The method includes receiving 820 using a communication interface, first data and second indicative of at least one measurement of at least one sensor component of the conformal sensor device. The conformal sensor device includes at least one sensor component to obtain the at least one measurement of a property of a temperature of the portion of the surface. The conformal sensor device substantially conforms to contours of the surface to provide a degree of conformal contact. The method includes, using a processing unit, computing 822 a first parameter indicative of a property of the temperature based on the degree of the conformal contact using the first data, and computing 824 a second parameter indicative of a property of the temperature based on the degree of the conformal contact using the second data. In block 826, the first parameter is compared to the second parameter, using the processing unit. The method includes (828) issuing a first notification if the first parameter exceeds the second parameter, and (830) issuing a second notification if the first parameter or the second parameter exceeds a preset threshold for at least a dwell time t. The first alert and/or the second alert provides an indication of a potential risk of harm to the object or individual.

Figure 8C:
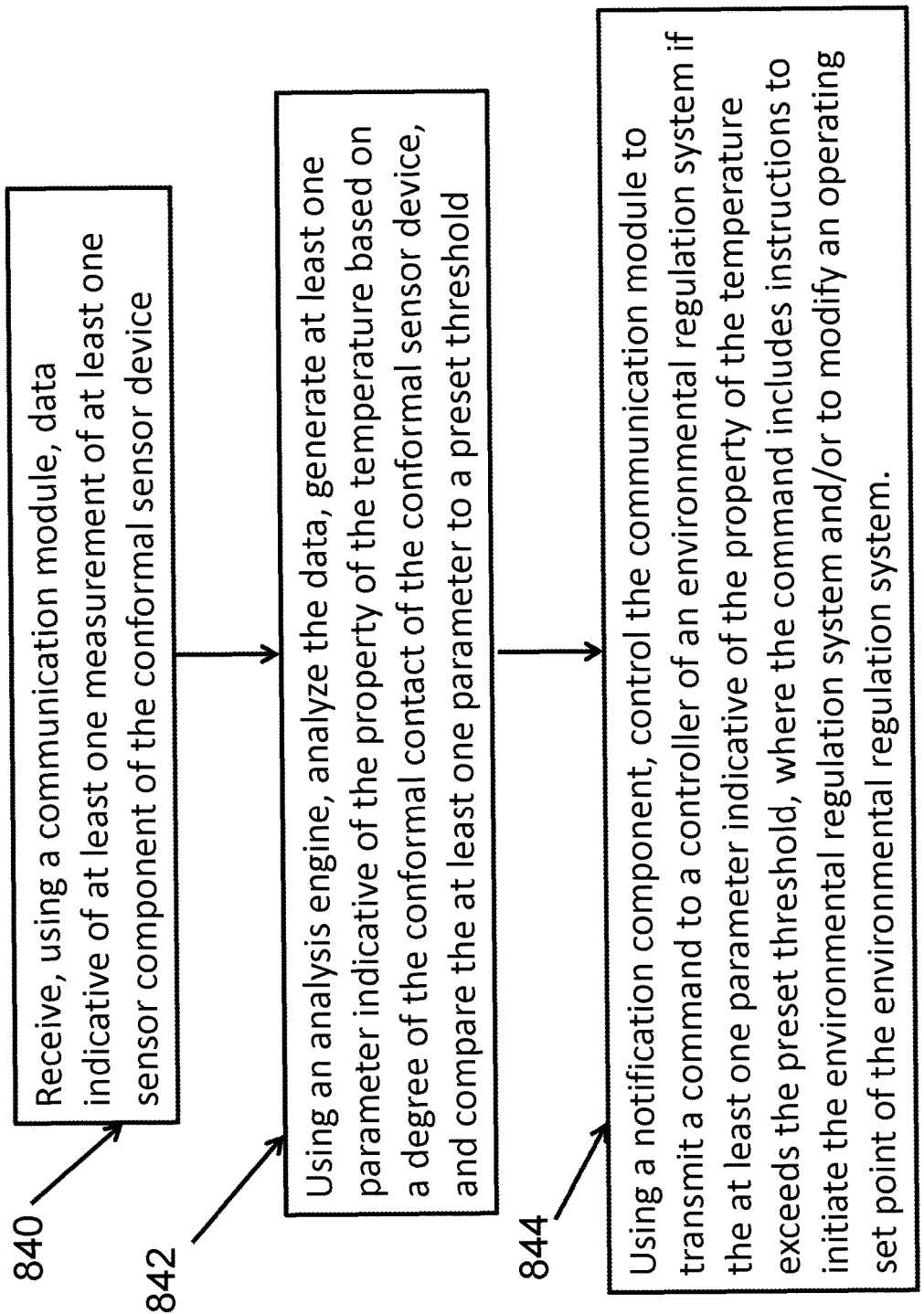
FIG. 8C shows a flowchart of another example method, according to the principles herein.

FIG. 8C shows an example method that can be implemented using any of the example systems, apparatus and devices herein. The example method can be used to regulate an environmental condition using a conformal sensor device mounted to a portion of a surface of the object or the individual. The method includes receiving 840 using a communication module, data indicative of at least one measurement of at least one sensor component of the conformal sensor device. The conformal sensor device includes at least one sensor component to obtain the at least one measurement of a property of a temperature of the portion of the surface. The conformal sensor device substantially conforms to contours of the surface to provide a degree of conformal contact. The method includes using 842 an analysis engine to analyze the data, to generate at least one parameter indicative of the property of the temperature based on a degree of the conformal contact of the conformal sensor device, and compare the at least one parameter to a preset threshold. The method includes using a notification component 844 to control the communication module to transmit a command to a controller of an environmental regulation system if the at least one parameter indicative of the property of the temperature exceeds the preset threshold. The command includes instructions to initiate the environmental regulation system and/or to modify an operating set point of the environmental regulation system.

Figure 8D:
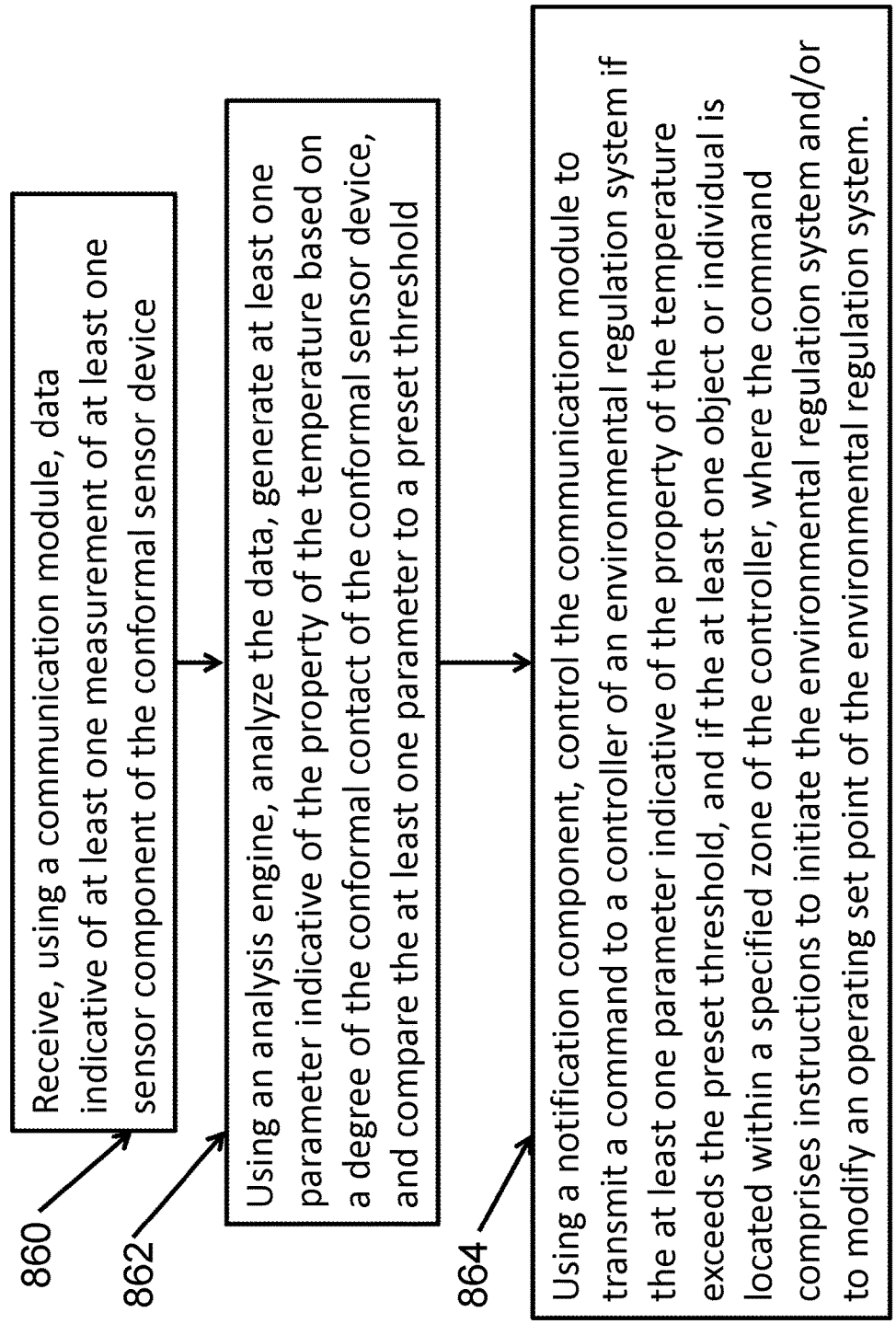
FIG. 8D shows a flowchart of another example method, according to the principles herein.

FIG. 8D shows an example method that can be implemented using any of the example systems, apparatus and devices herein. The example method can be used to regulate an environmental condition using a conformal sensor device mounted to a portion of a surface of the object or the individual. The method includes receiving 860 using a communication module, data indicative of at least one measurement of at least one sensor component of the conformal sensor device. The conformal sensor device includes at least one sensor component to obtain the at least one measurement of a property of a temperature of the portion of the surface. The conformal sensor device substantially conforms to contours of the surface to provide a degree of conformal contact. The method includes using 862 an analysis engine to analyze the data, to generate at least one parameter indicative of the property of the temperature based on a degree of the conformal contact of the conformal sensor device, and compare the at least one parameter to a preset threshold. The method includes using a notification component 864 to control the communication module to transmit a command to a controller of an environmental regulation system if the at least one parameter indicative of the property of the temperature exceeds the preset threshold, and if the at least one object or individual is located within a specified zone of the controller. The command includes instructions to initiate the environmental regulation system and/or to modify an operating set point of the environmental regulation system.

As a non-limiting example, the specified zone can be a specified distance. The instructions can specify the comparing of the location information to the specified distance to determine if the at least one object or individual is located within the specified zone. As non-limiting examples, the specified zone can be set as 0.5 mile, 1 mile, 2 miles, or more.

As another non-limiting example, the specified zone can be computed based on data representative of traffic conditions, including traffic speed and traffic route options.

In an example implementation, the system, method or apparatus can be configured to send a command with instructions to the environmental regulation system to heat or cool a room, e.g., in a house or apartment, when the individual is located with in the specified zone (e.g., while driving back), without need for the individual to place a call or otherwise initiate contact with the controller. The example system, method, apparatus can be configured to determine whether the individual is located within the specified zone based on traffic conditions, habitual schedule of the individual, and/or the conformal sensor readings of the individual.

Figure 8E:
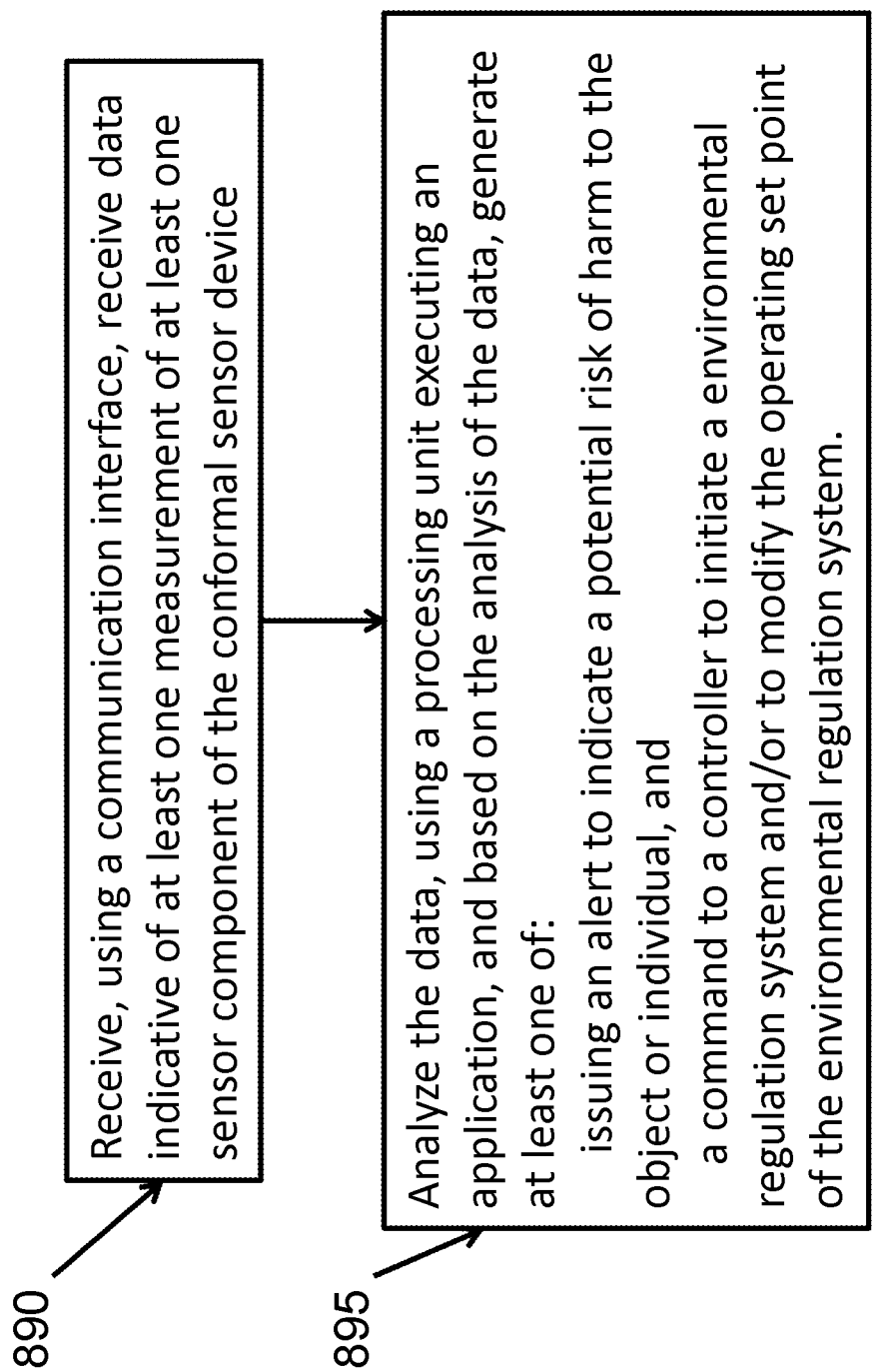
FIG. 8E shows a flowchart of another example method, according to the principles herein.

FIG. 8E shows an example method that can be implemented using any of the example systems, apparatus and devices herein. The example method can be used to monitor a property of an object or an individual using a conformal sensor device mounted to a portion of a surface of the object or the individual. The method includes receiving 890, using a communication interface, data indicative of at least one measurement of at least one sensor component of the conformal sensor device. The conformal sensor device includes at least one sensor component to obtain the at least one measurement of a property of a temperature of the portion of the surface. The conformal sensor device substantially conforms to contours of the surface to provide a degree of conformal contact. The method includes analyzing the data 895, using a processing unit executing an application, to generate at least one alert based on an analysis of the data. The alert provides an indication a potential risk of harm to the object or individual.

The example apparatus 300 shown in FIG. 3 also can be used to implement any of the example methods described in FIGS. 8A-8E.

Using the systems, methods, and apparatus described herein, data gathered based on sensing the temperature of the body or portion of the body (including tissue) can be analyzed to provide useful information related to the status of a user's body or the user's environment. In an example, a conformal sensor device can be used as a temperature sensor device. The conformal sensor device can be mounted to, or disposed proximate to, the body or portion of the body (including tissue). In an example, additional data gathered based on sensing other physiological measures of the body also can be analyzed to provide useful information related the status of a user's body or the user's environment.

In a non-limiting example, the conformal sensor device can be used to detect and/or monitor changes in temperature of at least a portion of a body of a human or a non-human animal. For example, the conformal sensor device herein can be used to detect and/or monitor elevated temperatures or associated changes in temperature, including temperatures associated with hyperthermia and/or a fever condition. As another example, the conformal sensor device herein can be used to detect and/or monitor depressed temperatures or associated changes in temperature, including temperatures associated with a hypothermia.

In any example according to the principles described herein, the at least one parameter can be a value of the temperature. The temperature can be quantified as an absolute value or as a relative value. For example, the temperature can be quantified relative to an average, median or mean temperature of a given subject or relative to an average, median or mean temperature of two or more subjects. In another example, the temperature can be quantified relative to a standard or other calibration. The standard or other calibration can be stored on the conformal sensor device or can be stored on an external system to which data from the conformal sensor device is transmitted or otherwise provided or exported.

When the sensing described herein is performed using thin, conformal, and wearable sensors and measurement devices including such sensors, these measures and metrics can be unimpeded by the size, weight or placement of the conformal sensor device measurement devices.

Example systems, methods, and apparatus according to the principles described herein provide a thin and conformal electronic measurement system capable of measuring the temperature of the body or portion of the body (including tissue) for a variety of applications, including rehabilitation, physical therapy, athletic training, and athlete monitoring. Additionally, the example systems, methods, and apparatus can be used for athlete assessment, performance monitoring, training, and performance improvement.

FIG. 9A-9D shows different components of an example system that includes an example conformal sensor device and accompanying peripheral devices for temperature detection and/or monitoring (including fever monitoring). In this non-limiting example, the conformable sensor device is configured as a reusable, conformable temperature sensor device.

Figure 9B:
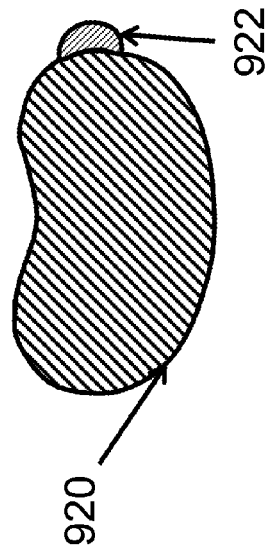
FIG. 9A-9D show components of an example system that includes an example conformal sensor device and accompanying peripheral devices, according to the principles herein.
Figure 9D:
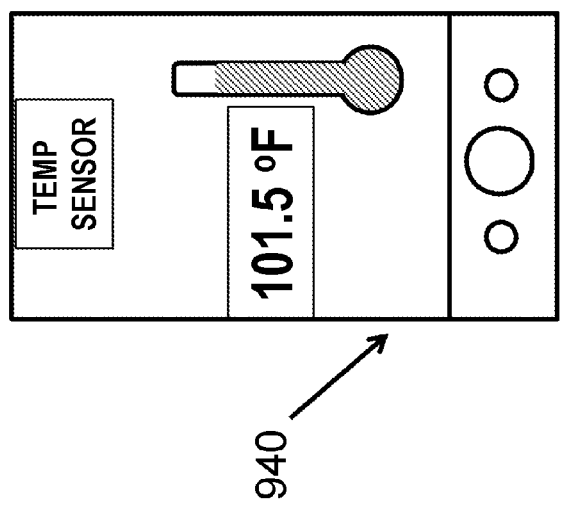
Figure 9A:
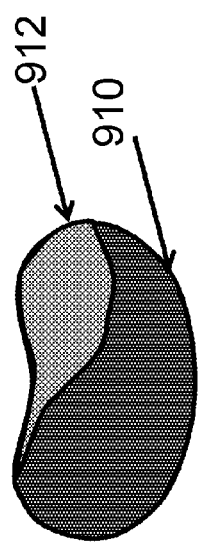

FIG. 9A shows a top view of the example conformal sensor device 910. The example conformal sensor device 910 can be coupled to a portion of an object or individual (e.g., on a body part) to continuously or intermittently monitor the temperature. For example, the example conformal sensor device 910 is configured to perform the measurements, either continuously or intermittently, to provide the data indicative of the property of the temperature. The data can be analyzed as described herein to provide the parameter indicative of the temperature.

A portion of the example conformal sensor device, such as but not limited to portion 912, can includes a portion configured to facilitate removal from a surface. For example, portion 912 can include somewhat more rigid edge handle(s) to facilitate easy peeling-off. Even though the major portion of the patch is flexible and hence conformal to the surface of the object or individual, at least one section of the conformal sensor device 910 can be configured to have a more rigid part that serves as a handle for wearers or other users to remove the conformal sensor device 910. Furthermore, this rigid handle portion can be the place where some rigid sensor components can be positioned.

FIG. 9B shows a top view of an example adhesive panel 920 that can be used to facilitate conformal coupling of the example conformal sensor device 910 to a portion of the surface of an object or an individual. The adhesive panel 920 can be a double-sided adhesive. Often times, a thin patch that fits and adheres to skin very well ends up being hard to peel off. The adhesive panel can include a tab 922 that coincides with rigid edge handle 912 and gives users a hold on the conformal sensor device 910 and remove it from the surface of the object or individual. The tab 922 may include an adhesive material or may be free of adhesive.

Figure 9C:
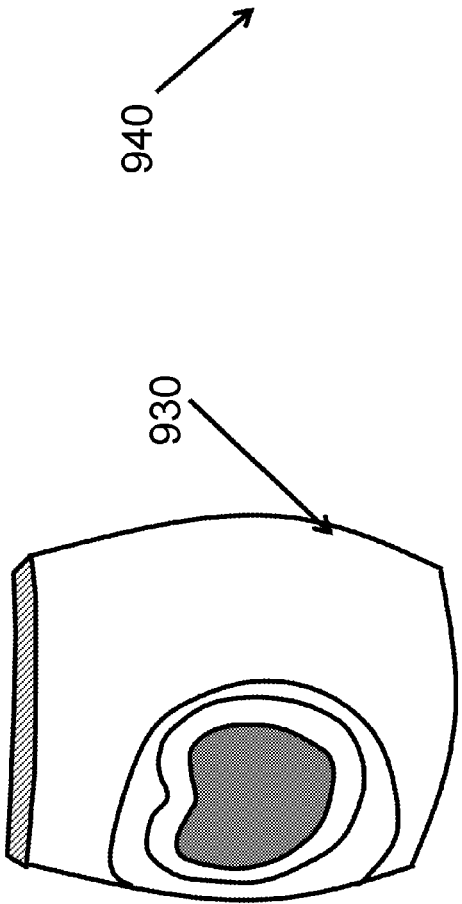

FIG. 9C shows an example charger 930 that can be used to charge a power source of the conformal sensor device 910. For example, the example charger can be configured to charge the conformal temperature sensor device via a standard AC wall plug. The charger also can include a compartment to store additional disposable adhesive panels 920.

FIG. 9D shows a display of an example App 940 that can be used to initiate the communication interface, analysis engine, and/or the notification component. The App 940 can be configured for any computing device described herein, such as but not limited to a smartphone or other handheld device. The example App 940 can be used to view the measurement data and/or the at least one parameter. For example, the temperature data can be displayed using the display of the App 940. The example App 940 also can be configured to present an input interface to allow a user to set the present threshold to which the at least one parameter is compared to determine whether and what type of alert is to be issued. For example, the temperature threshold can be used to determine whether an alarm is to be issued.

The example App 940 also can be used to provide information about the conformal sensor device and the patch layout. For example, the App can be configured to show a display of the different parts of the patch, the degree of conformal contact of the conformal sensor device and the patch, how they work, and information that a user can use to decide where to place and implement the conformal sensor device and the patch on-body or one an object.

The example App 940 also can be configured to show a display of the alert settings, including the preset threshold used to perform the comparisons (and issue the alerts). The example display can be configured to show a field on the display shows the current alert state.

Figure 10B:
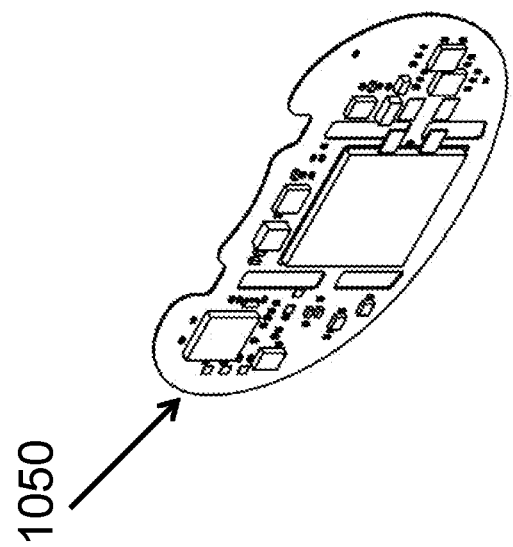
FIGS. 10A and 10B show exploded isometric view and an assembled view of a conformal sensor device, according to the principles herein.
Figure 10A:
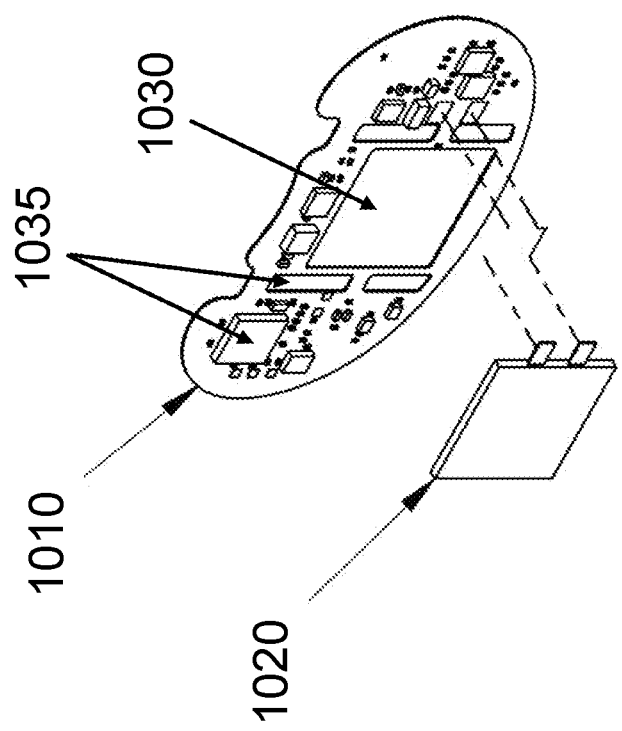

FIG. 10A shows an exploded isometric view of a base 1010 of an example conformal sensor device and a power source 1020 that is configured to be disposed in a designated section 1030 in the base 1010. FIG. 10A also shows other electronic components 1035 of the conformal sensor device, which includes the sensor component and at least one processing unit. FIG. 10B shows an assembled view 1050 of the conformal sensor device including the battery.

Figure 11:
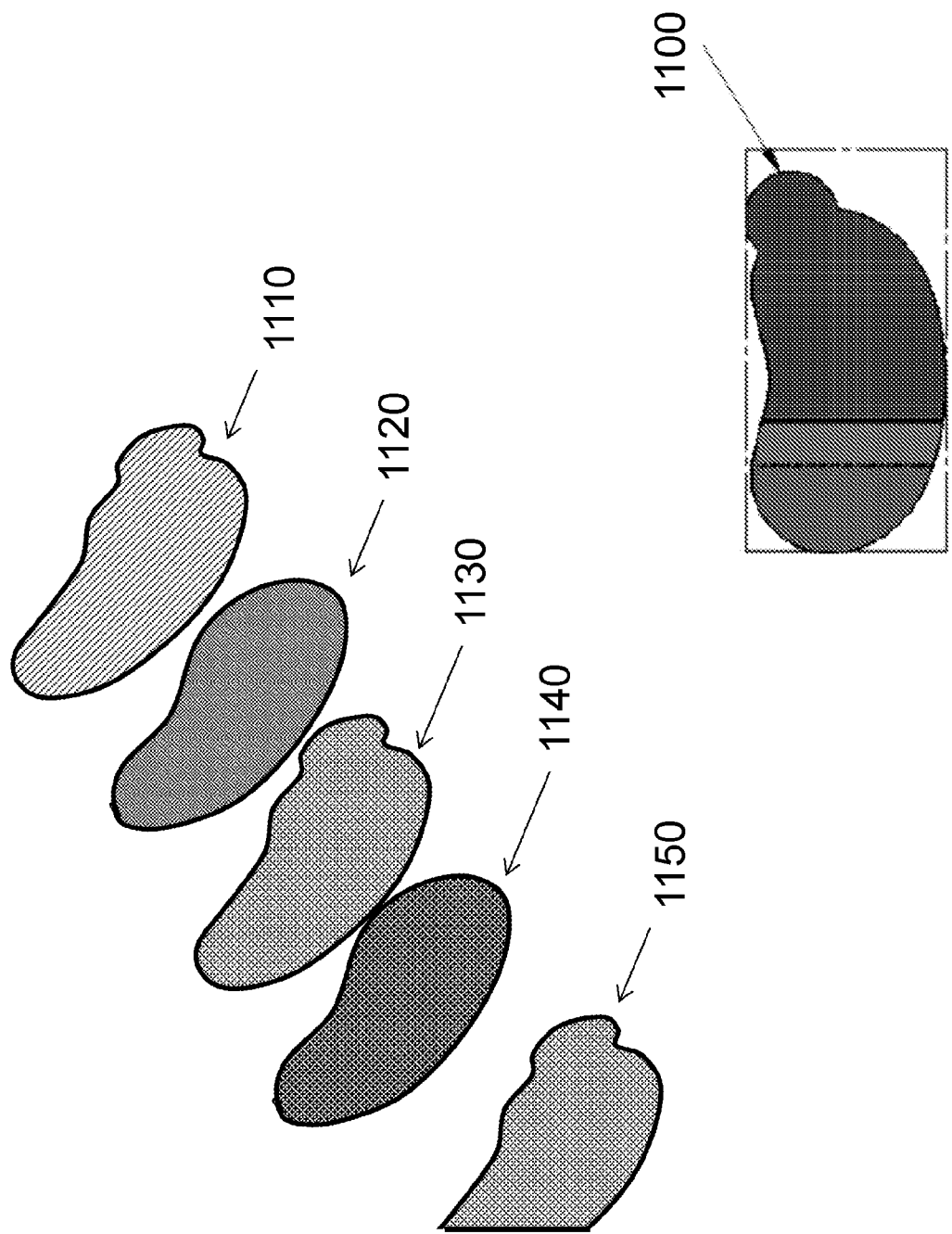
FIG. 11 shows an exploded view of an example adhesive panel, according to the principles herein.

FIG. 11 shows an exploded view of an example adhesive panel 1100. The example adhesive panel 1100 includes a first liner 1110, a first adhesive 1120, a carrier 1130, a second adhesive 1140, a second liner 1150.

Figure 12:
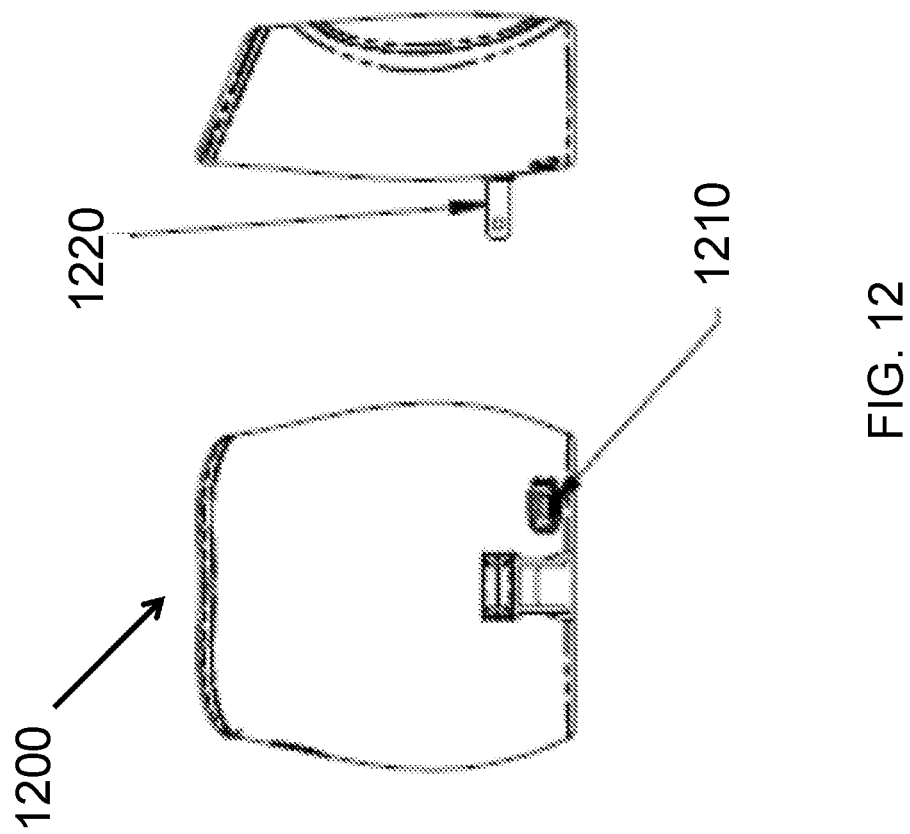
FIG. 12 shows a side view of an example charger, according to the principles herein.

FIG. 12 shows a side view of an example charger 1200. In various examples, the charger 1200 can include a USB connector 1210 and/or a plug 1220 to facilitate charging using the example charger 1200.

Figure 13:
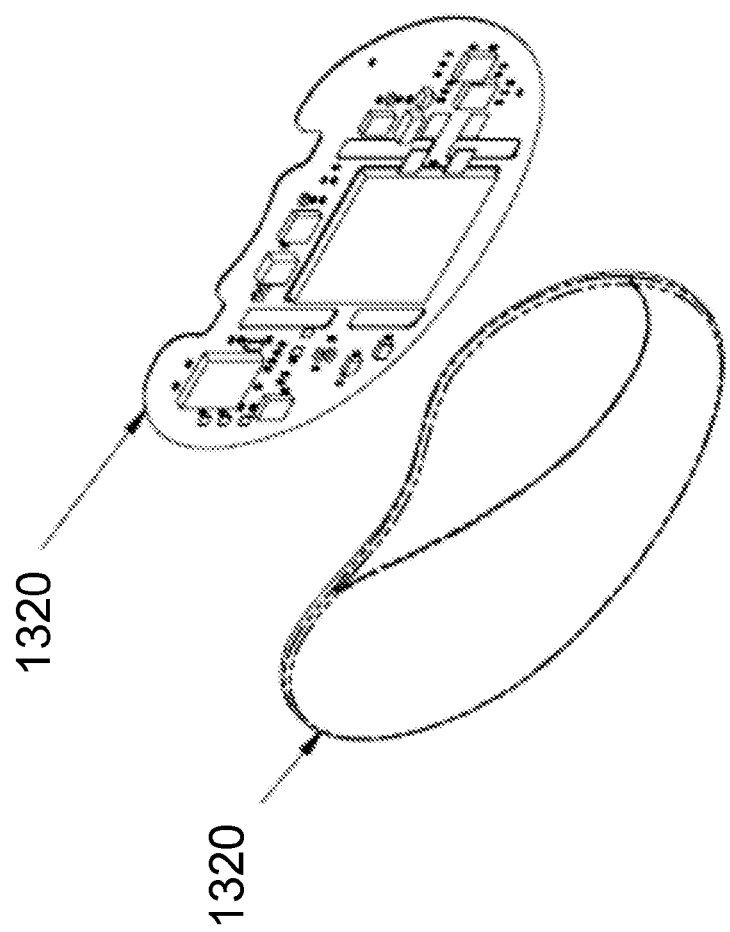
FIG. 13 shows an example encapsulation housing that can be coupled the conformal sensor device base, according to the principles herein.

FIG. 13 shows an encapsulation housing 1320 that can be coupled the conformal sensor device base 1320 to encapsulate the electronic components of the conformal sensor device base 1320.

The example conformal sensor device 910 can be configured to automatically measure and log body temperature-based measurement over a 12-hour period. The example conformal sensor device 910 can be configured to easily connect to an application for a smartphone or other hand-held device, on two smartphones (or other handheld devices). The example conformal sensor device 910 can be configured to measure temperature at a regular interval of 60 seconds. The example conformal sensor device 910 and App 940 for the smartphone or other hand-held device can be configured to support instant on-demand downloading and display of logged temperature data. The example conformal sensor device 910 can be configured to support user-defined high temperature threshold set point. The example App 940 can be configured to be intuitive.

The App 940 for the smartphone or other hand-held device can be configured to indicate if signal from patch is not being detected. The App 940 can be configured to display information on measurements (such as but not limited to an infant's body temperature) within a specified period of time of initiation of App 640 (such as but not limited to about 60 seconds of initiating the App 640). Example App 940 can be configured to enable user setting of temperature set point. Example App 940 can be configured to generate both a visual and an audio notification when temperature reaches or exceeds threshold set point for 5 minutes. Example App 940 can be configured to enable user to process the alarm by tapping an "off" button. Once the "OFF" button is tapped, if the temperature dips below the threshold, the alert setting can be set such that the alarm does not go off again until the temperature crosses and stays above the threshold for a period of time (about 5 minutes). If after hitting "off" the temperature stays above the threshold for a dwell time (e.g., about 5 more minutes), the App 940 is configured to cause the alarm to go off again.

Example App 940 can be configured to enable sharing user information to other friends, family, or medical providers (with informed consent). Example App 940 can be configured to be compatible with iPhone® 4S or iPhone®5 (Apple Inc.). Example App 940 can be configured to be Android™ compatible. Example App 940 can be configured to support software patches and upgrades. Example App 940 can be configured to automatically report software bugs.

The example conformal sensor device 910 can be configured to measure and log temperature data over a user-specified (such as but not limited to a 24-hour period). The example conformal sensor device 910 can be configured to cost less than about $35 to manufacture. The example conformal sensor device 910 can be configured to easily connect to example App 940 on multiple computing devices (including three smartphones or other handheld devices). Example App 940 can be configured to enable user setting of a temperature notification profile, such as ringtone, email message, SMS.

Example App 940 also can be configured to enable user-initiated logging of information on medicine administration, including one or more of: medicine type, amount, timestamp, types of allergy, potential drug interactions. Example App 940 can be configured to display medication administration information overlapped on temperature over time graph. Example App 940 can be configured to enable user setting of medicine administration notifications and reminders.

App 940 can be configured to display remaining battery life (in hours/minutes or with more meaningful symbols than battery icon). Example App 940 includes IFU's for medication, including but not limited to, baby Tylenol® (Johnson & Johnson, New Brunswick, N.J.), baby Motrin® (Pfizer Inc., New York, N.Y.) and baby Advil® (Pfizer Inc., New York, N.Y.). Example App 940 can be configured to enable creation and maintenance of discrete profiles for multiple children using the same patch (at different times). Example App 940 can be configured to enable creation and maintenance of discrete profiles for the same patch (each parent wants to set different parameters on his/her phone). Example App 940 can be configured to enable creation and maintenance of discrete profiles for multiple users (including children) using multiple patches (for example, 2+ kids in household sick at same time; twins/triplets). Example App 940 can be configured to support uploading of user identifying information (e.g., an infant's picture) to associate with profile.

The example conformal sensor device 910 can be configured to measure and log temperature data over a 48-hour period. The example conformal sensor device 910 can be configured to support more frequent transmission of temperature data once temperature crosses user-specified threshold. The example conformal sensor device 910 can be configured to support user-defined low temperature threshold set point. The example conformal sensor device 910 can be configured to support firmware updates through application for the smartphone or other hand-held device. The example conformal sensor device 910 can be configured to automatically transmit temperature data to example App 940 when temperature flux (rate of temperature change) exceeds pre-set rate. The example conformal sensor device 910 can be configured to support extensibility to additional temperature sensing and logging applications such as fertility (basal body temperature monitoring) and athletics (overheating). The example conformal sensor device 910 can be configured to easily connect to example App 940 on multiple computing devices (e.g., >3 smartphones (or other handheld devices).

The example charger 930 has sensors that measure room temperature, ambient humidity and other environmental indicators. The example charger functions as an audio or video baby monitor. Example App 940 can be configured to enable user opt-in or opt-out alerts to the example conformal sensor device 910, and recall notifications for medicines that the App supports. Example App 940 can be configured to enable user tracking of baby's immunization history. Example App 940 can be configured to enable user tracking of baby's nursing, drinking, eating, peeing and defecating, with a focus on times when the temperature sensor of the example conformal sensor device 910 is already being used because the baby is ill. Example App 940 can be configured to contain a calendar view that shows high-level overview of baby's information over a larger-time span than one patch. Example App 940 can be configured to enable user setting of a temperature data syndication service profile, RSS.

The example conformal sensor device 910 size and comfort profile can be configured to be suitable for infants. The example conformal sensor device 910 design can be configured to connote quality, comfort, and safety. The conformal sensor device can be configured to be appropriately flexible for on-the-body placement, and specifically for axillary placement. The example conformal sensor device 910 can be configured to be easy to disassemble (removing adhesive from sensor). The example conformal sensor device 910 can be configured to be easy to recharge.

The example conformal sensor device 910 can be configured to be very thin and conformable. The example conformal sensor device 910 can be configured to have a maximum thickness of about 2.6 mm and average thickness of less than about 2 mm. The example conformal sensor device 910 can be configured to be easy to clean and maintain clean appearance. The example conformal sensor device 910 can be configured to support usage lifetime of about 2 years. The example charger 930 can be configured to indicate when the conformal sensor device is fully charged. The example charger 930 can be configured to support charging both directly into a wall plug and with a cord. The example charger 930 can be configured to have night light functionality. Example App 940 can be configured to display temperature in one keystroke (taps). Example App 940 can be configured to show a graph of baby's temperature over time. Example App 940 can be configured to The example conformal sensor device 910 can be configured to meet technical requirements for use in the EU (including type of electrical outlet adaptors). The example conformal sensor device 910 can be configured to have an average thickness of less than 1.5 mm. The example charger 930 holds batteries to support charging and maintenance of charge without taking wall plug or countertop space.

The example conformal sensor device 910 can be configured to not cause excessive skin irritation or redness to baby's skin. The example conformal sensor device 910 removal can be configured to not exceed an acceptable level of discomfort.

The conformal temperature sensor device can be a battery-operated electronic device with possible use of measuring and monitoring human body temperature continuously or intermittently with periodic wireless transmission of temperature data which is utilized by the wireless receiver and the software application (on a smartphone, computer or tablet, or other hand-held device) to record, store, and display the temperature information. Temperature sensor contains a reusable temperature sensor and can be applied to the patient, e.g., by means of single use adhesive patches. Temperature sensor can be used for adults and children (through neonates).

The conformal temperature sensor device can be a battery-operated electronic device with possible use of measuring and monitoring human body temperature continuously or intermittently with periodic wireless transmission of temperature data which is utilized by the wireless receiver and the software application (on a smartphone, computer or tablet) to record, store, and display the temperature information. The conformal temperature sensor device contains a reusable temperature sensor and is applied to the patient by means of single use adhesive patches. Temperature sensor can be used for adults and children (through neonates).

Example App 940 can be configured to automatically record the conformal sensor measurements and/or other information about the object or individual, such as but not limited to a baby's temperature, medication history and other relevant information, if the analysis of the measurements and comparison to the preset threshold causes an alert to indicate the risk of potential harm (e.g., when a baby is sick).

The example conformal sensor device 910 can be configured to meet all applicable regulatory standards and requirements in the U.S. for FDA Approval The example conformal sensor device 910 can be configured to meet all applicable regulatory standards and requirements for CE Approval The example conformal sensor device 910 can be configured to be suitable for operation in a clinical environment The example conformal sensor device 910 can be configured to meet regulatory requirements in other regions outside Europe and the US The example conformal sensor device 910 can be configured to connect with home Wi-Fi network in an intuitive and fast manner.

The example conformal sensor device 910 can be configured to be suitable for operation in a home-use environment, with the range covering the majority of an averaged-sized, single-family home. The signal can be configured to reach from baby's crib to a parent's room at a minimum.

The example conformal sensor device 910 application (adhesive application to sensor and sensor application to body) can be configured to be intuitive and fast.

The example conformal sensor device 910 can be configured to have a lengthy self life, a maximum time between recharges (such as but not limited to about 6 month shelf life).

The example charger 930 can be configured to recharge sensor within a short period of time (such as but not limited to about 1 hour).

The example conformal sensor device 910 wireless signal range can be configured to cover an entire location (such as but not limited to an average-sized single family home).

Figure 14A:
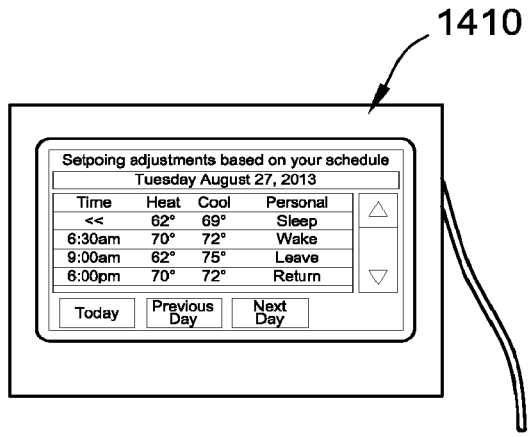
FIGS. 14A-14B show example controllers, according to the principles herein.

FIG. 14A shows an example interface of a controller 1410 of a building automation system to which instructions can be sent, based on the implementation of any example system, method or apparatus herein, to regulate an environmental condition.

Figure 14B:
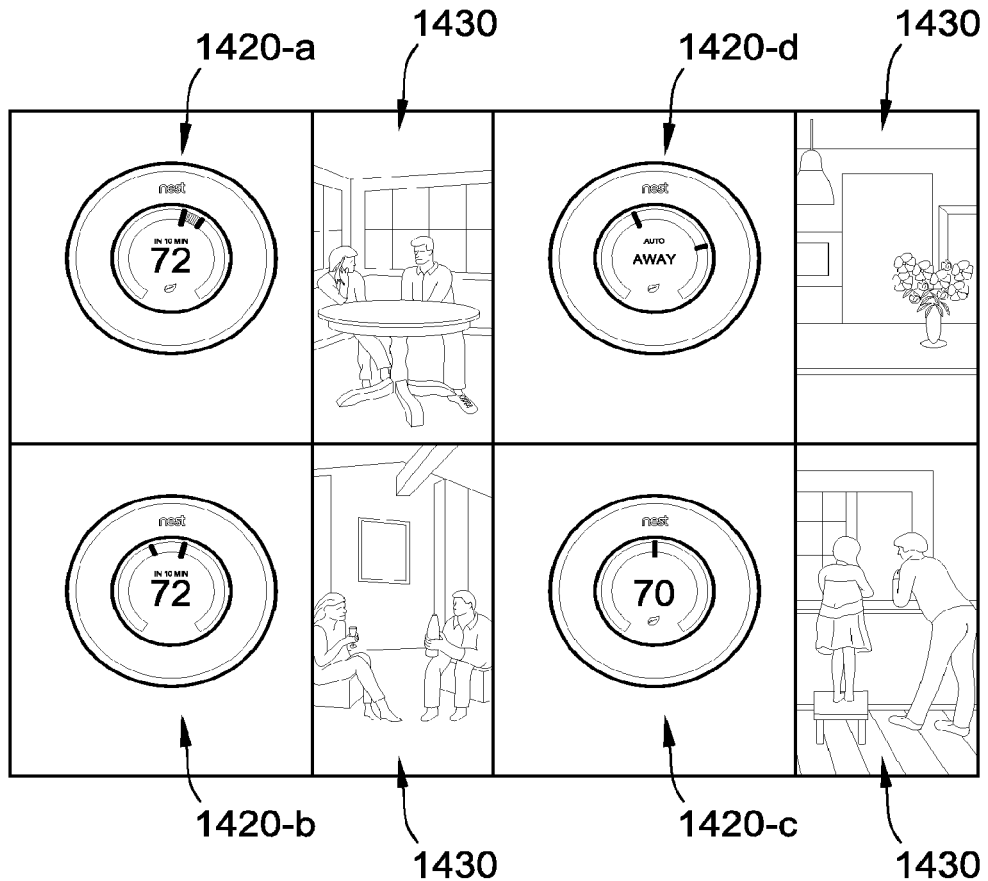

FIG. 14B shows an example implementation where the controllers are thermostats 1420-*a*, 1420-*b*, and 1420-*c* disposed in differing sections of a building. Data representative of measurements performed using conformal sensor devices coupled with any of the individuals 1430 in any of the rooms can be analyzed as described herein to generate the instructions to one or more of the thermostats 1420-*a*, 1420-*b*, and 1420-*c*. As described herein, differing portions of a building can be maintained at differing operating set points based on the analyzed measurement data from conformal sensor devices coupled with the individuals or objects in a given section of the building. The command to the controller of the environmental regulation system includes instructions to modify the operating set point as a function of time.

In an example implementation, the environmental regulation system is a HVAC, and the command to the controller of the environmental regulation system includes instructions to modify the operating set point of the HVAC of a building. In this example, the set point of the HVAC can be defined as the temperature at which the HVAC maintains the internal air temperature of the building. In any example, the set point can be a specified temperature (e.g., 20° C.), or can be a temperature range with an upper and lower bound of temperatures at which the HVAC is instructed to maintain the building (e.g., between 20° C. and 22° C.).

Each conformal sensor device can be configured with a transmission module to upload an historical data log based on the monitoring of the environmental conditions and/or the physiological measurement(s) of the object or individual associated with the conformal sensor device. When certain criteria are met, real time data can be pushed to the controller of the environmental regulation system as described herein.

In an example, the example systems, methods, or apparatus can be configured such that the controller (such as but not limited to the smart thermostat) and/or App of the computing device can transmit a signal acknowledging receipt of data from the conformal sensor device, so that the conformal sensor device can end the communication once such acknowledgment is received.

In an example, controller (such as but not limited to the smart thermostat) can be configured to adjust a set point of the environmental regulation system to adjust a climate-related settings (such as temperature and humidity) based on stored data (data log), stored values of the computed parameter, or the real parameter reading.

In an example, the conformal sensor component can be configured to include a wireless energy harvesting mechanism, such that the on-board energy source can be recharged wirelessly.

Non-Limiting Example Implementations Using Example Apps

Non-limiting example implementations of Apps on computing devices are described. While the Apps are described relative to a series of screenshots and navigation procedures, the subject matter herein is not so limited.

In the non-limiting example implementations described, Apps are described for use with an example conformal sensor device including at least one temperature sensor component. The example Apps can be configured as Android™ applications, or can be configured to run on other operating systems, including a iOS® operating system or a Windows® operating system.

Non-limiting example components and materials in the example implementations are as follows. The App can be used with a NFC-equipped, internet-connected hand-held computing device (such as but not limited to a Samsung Galaxy Note II®) operating the Android operating system. The App can be configured for download as a sensor App (a *.apk file).

Each different type of computing device running an Android™ operating system, or other operating system, may have a different NFC antenna size and/or location. There a certain amount of time, such as but not limited to about 10 minutes, about 15 minutes, about 20 minutes or more, can be taken to determine the optimal position and/or orientation of the computing device to ensure coupling (synchronization ("sync")) between the computing device and the patch including the conformal sensor device. An example App can be configured to show an animation requesting a user to "sync the sensor" to the computing device to find the optimal position and/or orientation. Transferring data from the conformal sensor device to the computing device may require a steady connection for a period of time. In any example implementation, the App may be configured to display "Sync Failed" messages to indicate a lack of proper coupling.

In an example implementation, once a successful sync has occurred, the App can be configured to prompt a user, e.g., with a pop-up, to perform at least one of showing the battery status, asking to name the sensor that is synchronized, enter information to specify parameters such as but not limited to a desired sampling frequency, a user's age, or a user's skin type.

The example App can be implemented to monitor a potential risk of harm to an object or individual and/or to regulate an environmental condition, as described herein.

Non-Limiting Example Implementations of the Conformal Sensor Devices

In an example, the conformal sensor device can be configured as a patch. The non-limiting example conformal sensor device can be mounted to, or disposed proximate to, a portion of a subject. For example, the conformal sensor device can be skin mounted. In an example, the conformal sensor device is configured as a conformal electronic device that allows it to be flexible and/or stretchable.

In a non-limiting example, a conformal sensor device can be configured according to the principles herein to employ different sensor types to measure and/or save data related to the status of the user's body or the user's environment.

In a non-limiting example, a conformal sensor device can be configured to transmit and/or receive information wirelessly or through a wired connection. For example, a non-limiting example conformal sensor device can be configured to communicate with a computing device, such as but not limited to a laptop or a hand-held device.

In a non-limiting example, the conformal sensor device can be configured to transmit and/or receive information via a Bluetooth® protocol, including a Bluetooth® Low Energy (BTLE) communication protocol. For example, the conformal sensor device can include a BTLE to WiFi communication relay when the computing device (such as but not limited to the hand-held device) is not within communication range of the conformal sensor device.

In any example, the conformal sensor device can be configured to transmit and/or receive information using any other communication protocol in the art.

As a non-limiting example, the conformal sensor device can be configured to include a conformal sensor device (serving as a thermometer patch).

In any example herein, the conformal sensor device can be configured as a FDA Class 2 medical device.

An example temperature sensor system according to the principles herein can be configured to couple to an inductive/WiFi bridge charging station.

In any example herein, the conformal sensor device can be configured to be mounted to a portion of a subject using an adhesive, such as but not limited to an adhesive sticker.

As a non-limiting example, the conformal sensor device can be fabricated on a soft, flexible, encapsulated, durable electronics module. As a non-limiting example, the fabrication can be according to a manufacturing process that includes one or more of wafer processing, SMT reflow, flex circuit assembly, flip chip bare die attachment, silicone encapsulation, and functional testing.

In an example implementation, an inductive/WiFi bridge charging station can be used to inductively charge the conformal sensor device.

An example conformal sensor device according to the principles herein can include an illumination source or an audible alert system. The illumination source or audible alert system can be used to issue any of the alerts described hereinabove. The illumination source also can serve as a built-in night light and/or can serve as a means for transmitting information related to the temperature data measured and/or stored by the conformal sensor device, or the analysis of such data. For example, a change in the level of illumination of the light source, or the color of the light source (such as but not limited to red, green, yellow), can be used to issue any of the alerts described hereinabove, including to indicate a change in temperature. In another example, any of the alerts described hereinabove, or any other information related to the temperature data or analysis of the temperature measurement data, can be communicated through blinking of the illumination source (according to an accepted communication protocol). The audible alter also can be similarly used to issue any of the alerts described hereinabove, including to indicate a change in temperature. For example, a change in the audible level of the alert or the tone of the audible alert, can be used to indicate an alert (including due to a change in temperature that exceeds a preset threshold). In another example, information related to the temperature data or analysis of the temperature data can be communicated through a change in the pattern of sound of the audible alert (according to an accepted communication protocol).

Non-Limiting Example of Acclimation Training

Systems, methods and apparatus according to the principles herein provide example conformal sensor devices that can be used to provide a measure of physiological signs including surface and core body temperature to provide monitoring for a training regimen designed to improve performance in specific climates. A soft thin and conformal device according to the principles described herein can be used to monitor body temperature and the data can be used to insure that activity levels cause surface or core body temperatures to remain above, at, or below certain specified values to insure higher performance in another climate at a different temperature including but not limited to altitude (pressure), humidity, temperature, as well as environmental conditions. Conditioning programs can be tailored to the individual by determining performance targets from the local environment to the target environment. In this way, athletes and other individuals wishing to improve performance can do so in one environment while training for another environment. In some cases, training at elevated temperatures can prepare the body for a wider range of targets temperatures in different environments.

As a non-limiting example, the conformal sensor device can be configured as a body-worn temperature patch, conformal and thin, and can be positioned in intimate contact with the body, or disposed proximate to the body, to provide up to date, and accurate measure of body temperature. Heat flux calculations can use data gathered by two or more such devices to provide an assessment of heat flux from one side to the other of the patch. Also temperature multiple patches and/or patches with multiple sensors can be used to provide measures of temperature data across the body to identify particular 'hot' zones of activity.

Non-Limiting Example of Predictive Temperature for High Exertion

While temperature, especially core temperature can provide signs or indicators of impending overheating or even dehydration, anticipating this through combined modalities, such as but not limited to temperature monitoring plus physiological data monitoring (including muscle activity monitoring) and/or motion sensing and analysis, can be used to give a better picture of direct activity leading to a temperature change. In this way, temperature changes and particular actions (drinking fluids, reducing activity) can be diagnosed and prescribed before they are anticipated. Anticipated blood flow and resultant sweat loss and temperature rise can be predicted/projected before the need to address these issues is greatest or becomes problematic (e.g., when the performance or hydration level of the subject falls below a predetermined threshold).

As motion and muscle activity rises, subsequent temperature change is anticipated and actions can be taken to mitigate issues related to this effect. An indicator communicate to the user or a coach or trainer whereupon actions such as changing clothing configurations, removing layers, opening vents etcetera can be made. In one example, a simple alert in the form of a light indicator, or a sound. Other means could be communication to a smart phone, which can alert the user. In addition, new types of clothing with forms of actuation to increase breathability of fabrics by responding to body heat or reacting to a signal to make clothing configuration modifications.

Elite athletes, amateur sports participants, and students athletes can benefit from highly optimized warm-up routines as well as in industrial settings such as construction, repair, military, that share comparable risks. See, e.g., Christian Cook, et al., "Designing a Warm-up Protocol for Elite Bob-skeleton Athletes, *International Journal of Sports Physiology and Performance*, Jun. 25, 2012. Heat stress and dehydration can be challenging in physiology that need to be solved related to health and safety risks, though both could benefit: warm-up routines (which can reduce chance of injury and improve performance) prioritized over sprint performance, though they might correlate, etc. As an example, there is no one temperature guideline across all humans.

As an example implementation of the systems, methods, and apparatus herein, the response of the conformal sensor device can be tailored to individual needs. Temperature thresholds and changes can vary from subject to subject, and person to person, so any system should take those variations into account by monitoring physiological parameters before, during, and after a workout. This can become a calibration process for a particular subject or person who would undertake a particular training or exercise activity to monitor body changes and outcomes to provide an assessment.

An example implementation of the systems, methods, and apparatus herein can be used for weight management. The patch-based device can be used to provide measurements that are correlated to changes in body temperature. Getting into shape can be correlated to changes in how the body reacts to exercise and core body temperature, using heat flux measurements, can provide this capability.

Core temperature (as a result of proper warm-up) can be linked to performance power output or explosiveness (e.g., short time for increased performance output). There is much evidence linking high body temperature to significant decrease in performance. But there is an intermediate range where performance is best; not too warm, and not too cool. Thus monitoring temperature to promote bursts of power for many sports applications such as football or sprinting can be important to performance in those examples.

In this example implementation, the alert described herein can be used to indicate a potential risk of harm to performance.

Non-Limiting Example of Tracking of Conditioning Level in Warm-Ups Prior to High Exertion Activities While the efficacy of warm-up activities prior to a high-exertion or athletic event can be beneficial, if too much time elapses between the warm-up and activities, the benefit disappears. By monitoring various parameters, including temperature, the state of the post warm-up activity can be monitored and action taken to insure continued readiness and maintained warm-up state. An example conformal sensor device according to the principles herein, combined with a secondary monitoring device, such as a stand-alone device or smartphone (or other computing device), can be used to monitor one or more subjects (such as people) to insure that the state of readiness is maintained. If the temperature or other parameter or set of parameters falls below a set threshold, warm-up activities can be engaged to stay in that state.

In this way, the beneficial aspects of warm-up can be maintained and peak performance is insured and injury likelihood can be reduced. See, e.g, Galazoulas et al, "Gradual decline in performance and changes in biochemical parameters of basketball players while resting after warm-up," *Eur J Appl Physiol* (2012) 112:3327-3334.

In this example implementation, the alert described herein can be used to indicate a potential risk of harm to performance.

Non-limiting Example Apparel with Integral Sensing that Reacts to Sensed Information Using Conformal Devices In another example, a conformal sensor device integrated with an article of apparel can be used to provide targeted capability for temperature control. Examples include a baseball pitcher, football quarterback, tennis or soccer where arms, shoulders or legs, depending on the position, can have actively temperature controlled with integrated heating elements whose control is a function of the body temperature which is measured through a conformal patch-based device.

In this example, locally sensed information such as body temperature and motion sensing and analysis can be used as a predictive means to anticipate changes in body temperature using one or more of the following sources of information including, but not limited to, temperature, motion, muscle activity, heart rate and heart rate variability, and respiration.

Non-Limiting Example of Linking a Suite of Sensing Modalities

In another embodiment, sensing modalities including but not limited to, motion and electromyography (EMG) are used to provide a more accurate and detailed assessment of body performance. In this way, a recording system that collects data from one or more sensors (of the same type or different types) can be used to correlate temperature change with activity. That, combined with environmental information about humidity, rain, temperature changes, pressure etc. can be used to create a detail model of how the body behaves under difference conditions and specific types of activity. For example, climbing outside on a mountain and then entering a cave may require equal physical exertion but the body may accommodate those environments different since environmental values can vary significantly from one environment to the next.

Heat stress, as one example, can be shown to be indicated by temperature and heart rate.

An example implementation of the systems, methods, and apparatus herein can be used to provide an alert of a potential risk of harm during active heating during warm ups, or during cooling down after the game.

Having sports players out of the training room and active and interacting with other people can be a benefit of having portable and wearable systems for selective heating and cooling. The monitoring systems can be built into the example conformal sensor device according to the principles herein (such as but not limited to the patches).

Non-Limiting Example of the Effects of Injury on Thermoregulation

The example conformal sensor devices according to the principles herein, such as but not limited to the patch-based systems, can be used to track local temperature changes and identify points of injury. During injury, blood flow can increase to that area, resulting to a change in temperature condition of the area. Thus, an example conformal sensor device herein can be configured to issue an alert, as described herein above, to identify the position of local injuries. In fact, blood flow to one area may cause shivering in another area. Thus, a temperature decrease in one area may reveal injury (and higher temperatures) in another area. The example conformal sensor devices according to the principles herein, such as but not limited to the patch-based systems, can include distributed temperature sensing modalities—such as but not limited to dense arrays of sensors, integrated into clothing or large area patches.

As a non-limiting example, for a swimsuit, a sharkskin hat, could integrate warm up activities. In this example, the conformal sensor device may include an energy storage device (such as but not limited to a battery pack) to warm areas. This can be used to maintain temperature, in a more active (as opposed to passive) form of thermoregulation.

As example can be seen in the influence of passive heat maintenance on lower body power output and repeated sprint performance in professional rugby league players. Kilduff L P, "The influence of passive heat maintenance on lower body power output and repeated sprint performance in professional rugby league players." J Sci Med Sport, 2012 Dec. 13, S1440-2440(12). Lower skin temperature can decrease maximal cycling performance. See, e.g., Imai D, "Lower skin temperature decreases maximal cycling performance," *Osaka City Med J.* 2011 December; 57(2):67-77. Warming-up and stretching can improve physical performance and prevent sports-related injuries. See, e.g., Shellock F G, "Warming-up and stretching for improved physical performance and prevention of sports-related injuries," *Sports Med.* 1985 July-August; 2(4):267-78. A conformal sensor device according to the principles herein can facilitate the implementation of the thermoregulation monitoring.

When used as part of a systematic conditioning program, an example conformal sensor device herein can be used to facilitate proper temperature regulation combined with other modalities and prescriptive conditioning. A temperature measurement using an example conformal sensor device described herein can be part of a program to provide several benefits, including injury prevention, athletic performance monitoring or improvement, monitoring of athletic explosive power output, and flexibility.

Physiological and Device Information Used in the Analysis of Temperature Data

Example systems, methods, and apparatus described herein can be implemented to monitor body temperature as a useful index to human performance. The example systems, methods, and apparatus described herein also can be used to monitor the performance of a non-human animal. In an example implementation, at least one alert can be issued as described herein in the event that a comparison of the at least one parameter to the preset threshold indicates that the object or individual is exhibiting too high a temperature. A condition of too high a temperature can be indicative of a risk of the potential harm of diminished performance.

For example, changes in body temperature can be a symptom of a performance-degrading problem. The potential harm can be, but is not limited to, hyperthermia or hypothermia. Each can be implicated where the comparison to the preset threshold indicates a change in core temperature that exceeds the acceptable range.

Sweat measurement and fluid loss can also be used to track performance and tracked to body performance. The potential harm of dehydration can cause degradation of the thermoregulatory ability of the body; resulting in a rise in core temperature. Accordingly, a conformal sensor herein can be used to monitor a potential risk of the harm of dehydration, and issue an alert based on the systems, methods and apparatus described herein. Also, a state of dehydration can be correlated with an increase in sweat loss and increased electrolyte concentration in sweat. In an example implementation, the conformal sensor device can include a hydration sensor to provide additional data that also can be analyzed to generate the at least one parameter.

In another example, physical stress and/or emotional stress also can be manifested via body temperature changes. Accordingly, a conformal sensor herein can be used to monitor a potential risk of the harm of physical stress and/or emotional stress, and issue an alert based on the systems, methods and apparatus described herein.

Several kinds of human performance limitations could involve temperature monitoring as part of the solution. An example system, method or apparatus herein can be used to provide real-time feedback, in the form of the alert(s), of a potential risk of harm. Using real-time feedback based on the alert(s) issued according to the analysis described herein, the environmental condition, behavior, activity level, or other condition of the object or individual can be changed. For example, the alert(s) can be issued to indicate that the object or individual is at risk of being in an excessively high-temperature environment (such as but not limited to a child or elderly person in a hot vehicle, or produce or fragile products in an unrefrigerated compartment. Based on the alert(s), the child or elderly person can be removed from the hot vehicle, or the refrigeration can be improved in the compartment to preserve the produce or fragile product.

In an example implementation, the example systems, methods, and apparatus can be used to monitor complex thermo-regulatory responses in the body. For example, a sharp drop in skin temperature at extremities during cold weather can reflect the diversion in the body of blood and other resources to maintain core temperature, and may not represent an immediate threat to performance. The measurement of the conformal sensor device can be used to indicate weather/wind conditions. The type of clothing and/or positioning of the conformal sensor device can affect the degree of conformal contact of the conformal sensor device. Strain on a temperature sensor can affect performance. The thin, conformal sensor devices described herein can be disposed with a degree of conformal contact that mitigates such strain.

Body impedance can change with activity. In an implementation, the example systems, methods, and apparatus can include an additional sensor component to measure body impedance as an additional sensing modality. The data from the impedance measurement can be includes in the analysis to generate the at least one parameter.

In an example, a user such as a sports-apparel company or other parties may can temperature monitoring according to the example systems, methods, and apparatus described herein to improve the performance of apparel and other products. For example, existing thermal apparel may be used to raise or lower core temperature by a certain number (N) degrees, but they do not provide data during wear. A temperature sensor based on a conformal sensor device herein can be used as a monitor to provide real-time feedback as to whether the apparel is successful at changing the temperature of the body of the individual but may not be addressing certain issues.

Non-Limiting Example of Regulation of an Environmental Condition

In an example implementation, the systems, methods and apparatus herein can be used to form a feedback loop that provides to data representative of the ambient temperature, humidity and/or other environmental data, as well as data representative of biometric-related parameters of the object or individual, to the analysis engine and notification component. Accordingly, the instructions to the controller of the environmental regulation system can be updated according to the analysis in the feedback loop.

In an example, the controller is a "smart thermostat."

In an example, the conformal sensor device can be formed as a patch, or any other form factor, that can be adhered to an object or individual (including the human body), and continuously monitor either the temperature of the object or individual, or ambient temperature proximate to the object or individual, to provide a feedback loop. Through wireless communication to the smart thermostat, the feedback loop is closed so that the smart thermostat can adjust temperature and other climate related settings based on the feedback.

Continuous monitoring and efficient communicating of biometric parameters using the conformal sensor device allows for integrating the automated measurement of the object or individual into the example system, method or apparatus.

In an example implementation, the conformal sensor device can be configured to be worn comfortable for periods of time each day (such as for many hours). In any such example, the conformal sensor device can include a memory to store the measurement data from the continuous monitoring as a continuous biometric parameter history log. In an example, the conformal sensor device can include an embedded non-volatile memory, such as a flash memory, an EEPROM, or a FeRAM, to store parameter historic data. Having such embedded memory also reduces the communication needs and helps with battery life. In any example, the system including the conformal sensor device can be configured for real-time monitoring.

The biometric parameters that can be measured using a conformal sensor device includes but is not limited to: temperature (both ambient and skin), humidity, pressure (both air and blood) and pulse.

The example conformal sensor device can be configured to communication with a computing device (including a smart phone) and/or a smart thermostat.

As described herein, each conformal sensor device can be recognized based on an ID component associated with a patch (e.g., a patch identifier). An example system, method and apparatus can include identifying and associating each different object or individual with each patch identifier.

In an example implementation, a conformal sensor device with an ID component can be configured to serve as an individual identifier that can be used to provide, for example, location based information through communication with smart home appliance and/or electronics whose locations are known. For example, the conformal sensor device can be used to locate individuals or objects (including a non-human animal) in an emergency, such as but not limited to a fire or smoke condition, a gas leak, etc. Individuals can have their location (i.e., which room they are in) communicated to other individuals or an emergency system through, for example, a smart fire/smoke detector in that room. In addition, the conformal sensor device can provide key information about the located individual, such as but not limited to, immediate ambient temperature, to help with rescue planning and decision making.

In an example implementation, activities and/or locations of senior citizens or other persons in assisted-living situations can be monitored using a conformal sensor device. In such an example, the conformal sensor device can be configured to provide continuous, continual or intermittent blood pressure and/or pulse monitoring, through communication between the conformal sensor device and a smart home health console.

Additional Attributes of the Technology

In any example system, methods or apparatus herein, a conformal sensor device may include one or more different types of sensor components to measure data indicative of a property of temperature. As non-limiting examples, the sensor components can include thermistor (including a negative temperature thermistor or a positive temperature thermistor), a thermocouple, a resistance thermometer (including a thin-film platinum resistance thermometer), a semiconductor-based temperature sensor (including a silicon bandgap temperature sensor or a p-n junction temperature sensor), an infrared temperature sensor, a chemical temperature sensor (e.g., based on a colorimetric change), or detection based on a temperature-coefficient frequency response of an oscillator (e.g., based on measurement of third harmonics).

In various example implementations, the conformal sensor devices can be disposed on or coupled to the skin or inserted in an ear of an individual, or can be disposed internally (e.g., by being ingested in a capsule form) to perform the at least one measurement. The skin-mounted conformal sensor device can be used to perform skin-temperature measurements or skin-based core temperature measurements.

In various example implementations, the measurements of the conformal sensor device can be subjected to differing types of information processing. For example, the sampling rate of the measurement data can be modified to improve the operational efficiency of the system. The data collection frequency and sample measurement frequency (how often the conformal sensor device performs a measurement) can affect the life of the power source of the conformal sensor device (e.g., the higher the frequency that is set, the shorter the battery life for a patch). In various examples, the conformal sensor device may be configured to enter intervals of sleep and wake cycles to increase power source lifetime. In an example, energy harvesting can be used to improve duration of the operation of the system including the conformal sensor device.

In various example implementations, the conformal sensor device can be configured as a patch, can be configured for apparel integration, can be configured as a separate strap-on device, can be configured for launderability, and/or can be configured for disposability.

In various example implementations, the conformal sensor device can be configured for use in applications such as but not limited to athlete training optimization, injury prevention, and/or patient care, according to the principles described herein.

In various example implementations, the conformal sensor device can be integrated with at least one physiological stress monitor, at least one hydration monitor, and/or as audio ear buds with integrated temperature sensing. For example, heart rate data can be used along with data indicative of core body temperature data to generate a measure of physiological stress.

For example, the audio ear buds can be integrated with an infrared temperature sensor to provide measurement values for core body temperature. In another example, the core body temperature can be determined from measurements of a skin-mounted patch.

CONCLUSION

While this specification contains many specific implementation details, these should not be construed as limitations on the scope of any inventions or of what may be claimed, but rather as descriptions of features specific to particular embodiments of the systems and methods described herein. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In some cases, the actions recited in the claims can be performed in a different order and still achieve desirable results. In addition, the processes depicted in the accompanying figures do not necessarily require the particular order shown, or sequential order, to achieve desirable results.

In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

What is claimed is:

1. A system comprising:
   a conformal sensor device mounted to a surface such that the conformal sensor device substantially conforms to contours of the surface, the conformal sensor device including a sensor component configured to generate data indicative of one or more measurements of a property of a temperature of a portion of the surface, and a stretchable electrical interconnect that electrically couples the sensor component to another component of the conformal sensor device;
   an analysis engine configured to analyze the data indicative of the one or more measurements of the property of the temperature of the portion of the surface to determine the property of the temperature of the portion of the surface;
   a notification component configured to (i) issue an alert in response to the property of the temperature exceeding a preset threshold for a dwell time and (ii) transmit a command in response to the property of the temperature exceeding the preset threshold; and
   a controller of an environmental regulation system configured to (i) receive the command from the notification component and (ii) execute a pre-determined action based on the received command.

2. The system of claim 1, wherein the dwell time is about three minutes, about five minutes, about eight minutes, or about ten minutes.

3. The system of claim 1, wherein the property of the temperature includes a magnitude, a spatial gradient, or a rate of change with time.

4. The system of claim 1, further comprising a display configured to display information related to the measurement of the property of the temperature.

5. The system of claim 1, wherein the conformal sensor device further includes a flexible substrate, the sensor component being disposed on the flexible substrate.

6. The system of claim 1, wherein the conformal sensor device further includes a stretchable substrate, the sensor component being disposed on the stretchable substrate.

7. The system of claim 1, wherein the conformal sensor device further includes a second sensor component configured to generate data indicative of one or more measurements of a property of a temperature of an environment adjacent to the portion of the surface.

8. The system of claim 7, wherein the first sensor component faces towards the surface and the second sensor component faces away from the surface.

9. The system of claim 1, wherein the notification component is configured to transmit the data indicative of the one or more measurements of the property of the temperature, receive the data indicative of the one or more measurements of the property of the temperature, or both transmit and receive the data indicative of the one or more measurements of the property of the temperature.

10. The system of claim 1, wherein the analysis engine is configured to compare the property of the temperature with a pre-defined standard.

11. The system of claim 10, wherein the analysis engine is disposed on a device external to the conformal sensor device.

12. The system of claim 10, wherein the analysis engine determines a measure of core body temperature as a function of the comparison of the property of the temperature and the pre-defined standard.

13. The system of claim 1, wherein the sensor component is part of a spatially-distributed array of sensor components configured to perform the one or more measurements of the property of the temperature of the portion of the surface.

14. The system of claim 13, wherein the measured property of the temperature is a spatial temperature gradient between two or more of the sensor components in the spatially-distributed array of sensor components.

15. The system of claim 14, wherein the spatial temperature gradient indicates information about a degree of conformal contact between the conformal sensor device and the contours of the surface.

16. The system of claim 15, wherein the information includes a spatial mapping of the degree of conformal contact as a function of the spatial temperature gradient.

17. The system of claim 1, wherein the surface is tissue, and wherein the conformal sensor device includes a second sensor component configured to generate data indicative of one or more measurements of electrical properties of the tissue.

18. The system of claim 17, wherein the one or more measurements of the electrical properties of the tissue includes a capacitive-based measurement.

19. The system of claim 17, wherein the system determines a hydration level of the tissue as a function of the measured electrical properties of the tissue.

20. The system of claim 17, wherein the notification component is further configured to issue an alert based on the hydration level of the tissue.

21. The system of claim 20, wherein the alert is issued if the hydration level of the tissue falls below a predetermined threshold.

22. The system of claim 14, wherein the spatial temperature gradient indicates blood flow.

23. The system of claim 14, wherein the spatial temperature gradient indicates a location of an injury.

24. The system of claim 1, wherein the property of the temperature is a spatial gradient that is indicative of blood flow.

25. The system of claim 1, wherein the command to the controller comprises instructions to initiate the environmental regulation system.

26. The system of claim 1, wherein the command to the controller comprises instructions to modify an operating set point of the environmental regulation system.

27. The system of claim 1, wherein the conformal sensor device includes an identification component configured to provide identification information associated with an individual.

28. The system of claim 27, further comprising a location component capable of communicating with the identification component, wherein the analysis engine determines a location of the conformal sensor device relative to the location component based on communication between the location component and the identification component.

29. The system of claim 28, wherein the analysis engine computes location information associated with the individual based on the location of the conformal sensor device relative to the location component, a known location of the location component, and a known communication distance of the location component.

30. The system of claim 29, wherein the computed location information associated with the individual and the identification information associated with the individual are transmitted to the controller of the environmental regulation system.

31. A system comprising a plurality of conformal sensor devices mounted to a surface such that each of the plurality of conformal sensor devices substantially conforms to contours of the surface, each of the plurality of conformal sensor devices including a sensor component, the sensor components of the plurality of conformal sensor device being configured to determine a spatial temperature gradient of a portion of the surface.

32. The system of claim 31, wherein the spatial temperature gradient indicates blood flow.

33. The system of claim 31, wherein the spatial temperature gradient indicates a location of an injury adjacent to the surface.

34. The system of claim 33, further comprising a notification component configured to issue an alert to identify the location of the injury.

35. The system of claim 34, wherein each of the plurality of conformal sensor devices is a separate and distinct patch and the surface is human skin.

* * * * *